United States Patent
McDevitt et al.

(10) Patent No.: US 6,647,549 B2
(45) Date of Patent: Nov. 18, 2003

(54) FINGER GLOVE

(75) Inventors: Jason P. McDevitt, Alpharetta, GA (US); Michael S. Brunner, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/826,413

(22) Filed: Apr. 4, 2001

(65) Prior Publication Data

US 2002/0152538 A1 Oct. 24, 2002

Related U.S. Application Data

(60) Provisional application No. 60/195,517, filed on Apr. 6, 2000, provisional application No. 60/195,071, filed on Apr. 6, 2000, provisional application No. 60/194,929, filed on Apr. 6, 2000, provisional application No. 60/195,072, filed on Apr. 6, 2000, provisional application No. 60/194,930, filed on Apr. 6, 2000, and provisional application No. 60/257,137, filed on Dec. 20, 2000.

(51) Int. Cl.[7] .................... A41D 13/00; A41D 19/00; B08B 1/00

(52) U.S. Cl. .............. 2/21; 2/167; 15/104.94; 15/167.1; 15/227; 401/7

(58) Field of Search ................ 2/21, 163, 158, 2/159, 167; 401/7; 15/104.93, 104.94, 167.1, 227; 433/42, 216

(56) References Cited

U.S. PATENT DOCUMENTS

| | | | |
|---|---|---|---|
| 1,896,941 A | 2/1933 | Cohen | |
| 2,076,681 A | 4/1937 | Steinmayer | |
| 2,122,482 A | 7/1938 | Marr et al. | |
| 2,179,614 A | 11/1939 | Cohen | |
| 2,673,365 A | * 3/1954 | Diveley | ....................... 15/215 |

(List continued on next page.)

FOREIGN PATENT DOCUMENTS

| | | | |
|---|---|---|---|
| EP | 0303528 | 7/1988 | |
| EP | 638277 A1 | * 2/1995 | ........... A47L/13/18 |
| EP | 0985364 A2 | 3/2000 | |
| EP | 0985364 A3 | 3/2000 | |
| EP | 0985364 B1 | 1/2002 | |
| GB | 2099305 A | * 12/1982 | ........... A61C/15/00 |
| GB | 2227938 A | * 8/1990 | ........... A61C/15/00 |
| WO | WO 87/07122 | 12/1987 | |
| WO | WO 92/03947 | 3/1992 | |
| WO | WO 95/31154 | 11/1995 | |
| WO | WO 99/55271 | 11/1999 | |

OTHER PUBLICATIONS

Medical Textiles, Nov. 1999 "Crimped Bristle Toothbrush". "Nonwoven Removes Stains", "Dental Floss".
Tetra Medical Supply Corp.; Product Information; Jan. 4, 2000; www.tetramed.com/dress.htm.
Spandage; Product Information; Jan. 4, 2000; spandage.com/main.htm.
FootSmark Products; Product Information–Toe Caps & DigiCushions; Jan. 4, 2000; www.footsmart.com.
JP05044165 English Abstract.

(List continued on next page.)

Primary Examiner—Rodney M. Lindsey
(74) Attorney, Agent, or Firm—Dority & Manning, P.A.

(57) ABSTRACT

A finger glove that can fit onto a human finger is provided. The finger glove can be used as a substitute for cotton balls, swabs, and/or gauzes, or as an oral cleaning device. The finger glove is at least partially made from an elastomeric material such that the glove can more aptly fit onto a finger. Moreover, the glove can also be partially made from a texturized material having an abrasive surface useful for cleaning surfaces. Furthermore, the glove, in some instances, can possess a barrier that is liquid-impermeable, but vapor-permeable so that the finger of a user is more comfortable during use. Various additives can be applied to the glove.

30 Claims, 9 Drawing Sheets

U.S. PATENT DOCUMENTS

| | | | |
|---|---|---|---|
| 2,882,528 A | * 4/1959 | Tassie | 2/21 |
| 2,925,605 A | * 2/1960 | Wheeler | 2/21 |
| 3,070,102 A | 12/1962 | MacDonald | |
| 3,124,824 A | * 3/1964 | Lutz | 15/227 |
| 3,263,681 A | * 8/1966 | Nechtow et al. | 2/21 |
| 3,298,507 A | 1/1967 | Micciche | |
| 3,338,992 A | 8/1967 | Kinney | |
| 3,341,394 A | 9/1967 | Kinney | |
| 3,368,668 A | * 2/1968 | Micciche | 206/229 |
| 3,448,478 A | * 6/1969 | Nash et al. | 15/104.93 |
| 3,485,706 A | 12/1969 | Evans | |
| 3,502,763 A | 3/1970 | Hartman | |
| 3,542,615 A | 11/1970 | Dobo et al. | |
| 3,589,823 A | 6/1971 | Hendrickson | |
| 3,675,264 A | * 7/1972 | Storandt | 15/104.94 |
| 3,692,618 A | 9/1972 | Dorschner | |
| 3,802,817 A | 4/1974 | Matsuki et al. | |
| 3,849,241 A | 11/1974 | Butin et al. | |
| 3,853,412 A | 12/1974 | Griffin | |
| 3,855,046 A | 12/1974 | Hansen et al. | |
| 3,902,509 A | 9/1975 | Tundermann et al. | |
| 3,905,113 A | 9/1975 | Jacob | |
| 3,952,867 A | 4/1976 | McCord | |
| 4,041,203 A | 8/1977 | Brock et al. | |
| 4,084,586 A | 4/1978 | Hettick | |
| 4,269,181 A | 5/1981 | Delannoy | |
| 4,323,534 A | 4/1982 | DesMarais | |
| 4,335,731 A | * 6/1982 | Bora, Jr. | 433/216 |
| 4,340,563 A | 7/1982 | Appel et al. | |
| 4,414,970 A | 11/1983 | Berry | |
| 4,616,374 A | 10/1986 | Novogrodsky | |
| 4,617,694 A | 10/1986 | Bori | |
| 4,643,725 A | 2/1987 | Schlesser et al. | |
| 4,643,791 A | 2/1987 | Jurrius et al. | |
| 4,655,760 A | 4/1987 | Morman et al. | |
| 4,657,802 A | 4/1987 | Morman et al. | |
| 4,660,228 A | * 4/1987 | Ogawa et al. | 2/167 |
| 4,663,220 A | 5/1987 | Wisneski et al. | |
| 4,665,901 A | * 5/1987 | Spector | 601/139 |
| 4,707,398 A | 11/1987 | Boggs | |
| 4,720,415 A | 1/1988 | Vander Wielen et al. | |
| 4,724,184 A | 2/1988 | Killian et al. | |
| 4,733,410 A | 3/1988 | Glotkin | |
| 4,741,949 A | 5/1988 | Morman et al. | |
| 4,766,029 A | 8/1988 | Brock et al. | |
| 4,781,966 A | 11/1988 | Taylor | |
| 4,789,699 A | 12/1988 | Kieffer et al. | |
| 4,795,668 A | 1/1989 | Krueger et al. | |
| 4,803,117 A | 2/1989 | Daponte | |
| 4,820,572 A | 4/1989 | Killian et al. | |
| 4,825,470 A | 5/1989 | Horio | |
| 4,828,556 A | 5/1989 | Braun et al. | |
| 4,834,738 A | 5/1989 | Kielpikowski et al. | |
| 4,858,245 A | 8/1989 | Sullivan et al. | |
| 4,875,247 A | 10/1989 | Berg | |
| 4,920,974 A | 5/1990 | Roth et al. | |
| 4,923,742 A | 5/1990 | Killian et al. | |
| 4,926,851 A | 5/1990 | Bulley | |
| 4,965,122 A | 10/1990 | Morman | |
| D313,317 S | 1/1991 | Brunner et al. | |
| 4,981,747 A | 1/1991 | Morman | |
| 4,998,978 A | 3/1991 | Varum | |
| 5,036,551 A | * 8/1991 | Dailey et al. | 2/167 |
| 5,057,368 A | 10/1991 | Largman et al. | |
| 5,068,941 A | 12/1991 | Dunn | |
| 5,093,422 A | 3/1992 | Himes | |
| 5,108,820 A | 4/1992 | Kaneko et al. | |
| 5,108,827 A | 4/1992 | Gessner | |
| 5,114,781 A | 5/1992 | Morman | |
| 5,116,662 A | 5/1992 | Morman | |
| 5,120,758 A | 6/1992 | Satoh | |
| 5,123,113 A | 6/1992 | Smith | |
| 5,133,971 A | 7/1992 | Copelan et al. | |
| 5,169,706 A | 12/1992 | Collier, IV et al. | |
| 5,213,428 A | 5/1993 | Salman | |
| 5,226,992 A | 7/1993 | Morman | |
| 5,228,433 A | 7/1993 | Rosen | |
| 5,277,976 A | 1/1994 | Hogle et al. | |
| 5,287,584 A | 2/1994 | Skinner | |
| 5,294,482 A | 3/1994 | Gessner | |
| 5,304,599 A | 4/1994 | Himes | |
| 5,332,613 A | 7/1994 | Taylor et al. | |
| 5,336,545 A | 8/1994 | Morman | |
| 5,336,552 A | 8/1994 | Strack et al. | |
| 5,348,153 A | 9/1994 | Cole | |
| 5,356,005 A | 10/1994 | Burrello | |
| 5,382,400 A | 1/1995 | Pike et al. | |
| 5,383,846 A | 1/1995 | Short | |
| 5,389,202 A | 2/1995 | Everhart et al. | |
| 5,439,487 A | * 8/1995 | Stanitzok | 15/227 |
| 5,440,774 A | 8/1995 | Cole | |
| 5,445,825 A | 8/1995 | Copelan et al. | |
| 5,464,688 A | 11/1995 | Timmons et al. | |
| 5,466,410 A | 11/1995 | Hills | |
| 5,474,525 A | 12/1995 | Blott | |
| 5,486,381 A | 1/1996 | Cleveland et al. | |
| 5,487,201 A | 1/1996 | Hansen et al. | |
| 5,502,863 A | 4/1996 | Perkins | |
| 5,503,908 A | 4/1996 | Faass | |
| 5,507,641 A | 4/1996 | Cline | |
| 5,524,764 A | 6/1996 | Kaufman et al. | |
| 5,529,665 A | 6/1996 | Kaun | |
| 5,541,388 A | 7/1996 | Gadd | |
| 5,554,076 A | * 9/1996 | Clark | 473/61 |
| 5,591,510 A | 1/1997 | Junker et al. | |
| 5,636,405 A | 6/1997 | Stone et al. | |
| 5,678,273 A | 10/1997 | Porcelli | |
| 5,765,252 A | 6/1998 | Carr | |
| 5,766,248 A | * 6/1998 | Donovan | 606/1 |
| 5,771,522 A | * 6/1998 | Carmody | 15/208 |
| 5,794,774 A | 8/1998 | Porcelli | |
| 5,819,765 A | 10/1998 | Mittiga | |
| 5,826,599 A | 10/1998 | Adams | |
| 5,834,002 A | 11/1998 | Athanikar | |
| 5,875,513 A | 3/1999 | Reinold | |
| 5,909,739 A | 6/1999 | Masrour-Rad | |
| 5,911,319 A | 6/1999 | Porcelli et al. | |
| 5,953,783 A | 9/1999 | Hahn | |
| 6,019,773 A | 2/2000 | Denmark | |
| 6,105,587 A | 8/2000 | Dunn | |
| 6,112,356 A | 9/2000 | Hashey | |
| 6,139,514 A | 10/2000 | Benson | |
| 6,494,767 B2 | * 12/2000 | Fisher | 451/28 |
| 6,336,461 B1 | 1/2002 | Martinez | |
| 6,409,059 B1 | 6/2002 | Calvert | |
| 6,420,625 B1 | * 7/2002 | Jones et al. | 604/367 |
| 6,508,602 B1 | * 1/2003 | Gruenbacher et al. | 401/7 |
| 2002/0170133 A1 | * 11/2002 | McDevitt et al. | 15/167.1 |

OTHER PUBLICATIONS

JP06205723 English Abstract.

JP06285108 English Abstract.

European Search Report; KCX–247–PCT; Int'l App. No. PCT/US 01/11172; Dec. 14, 2001.

Abstract of Japanese Patent No. 10243818 Sep. 14, 1998.

U.S. patent application Ser. No. 09/826,371, McDevitt et al., filed Apr. 4, 2001.

* cited by examiner

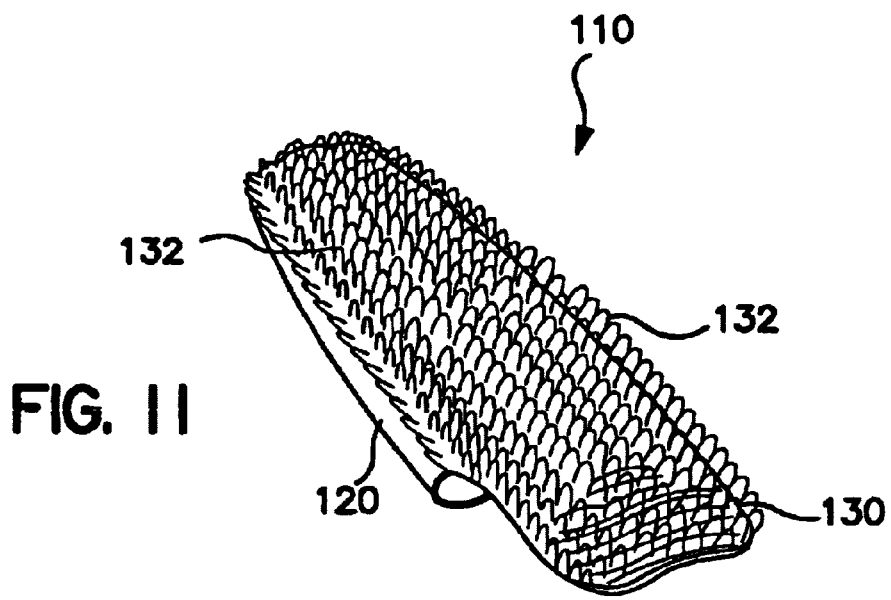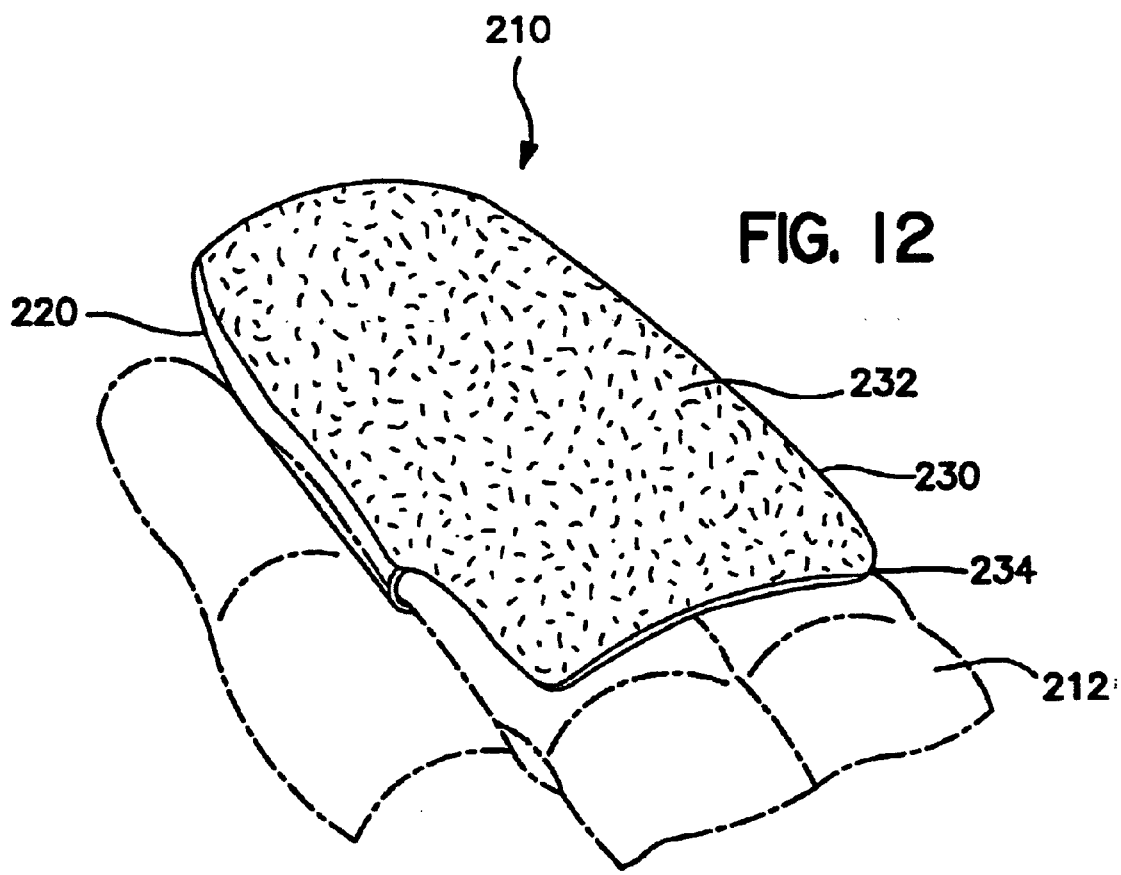

FINGER GLOVE

RELATED APPLICATIONS

This application is based upon and claims priority to the following provisional applications:

U.S. Ser. No. 60/195,517, filed on Apr. 6, 2000; U.S. Ser. No. 60/195,071, filed on Apr. 6, 2000; U.S. Ser. No. 60/194,929, filed on Apr. 6, 2000; U.S. Ser. No. 60/195,072, filed on Apr. 6, 2000; U.S. Ser. No. 60/194,930, filed on Apr. 6, 2000; and U.S. Ser. No. 60/257,137, filed on Dec. 20, 2000.

BACKGROUND OF THE INVENTION

Cotton balls, swabs, and gauzes are commonly used for a variety of reasons. For instance, a cotton ball can be used to apply diaper rash ointments, medications, alcohol, oral anesthetics, etc. Moreover, in some cases, a cotton ball can also be utilized to remove various types of materials from a person, such as, for example, facial make-up. In each of these fields, the cotton ball or swab is typically configured to deliver a particular additive or ingredient to the area of application.

However, in some instances, it may be difficult for a user to apply an additive to a cotton ball, for example, without undesirably spilling some of the additive. Moreover, cotton materials can often be relatively expensive and difficult to process in comparison to other types of materials. As such, a need currently exists for an improved product capable of delivering an additive, such as a medication, to a particular area of application. In particular, a need currently exists for a finger glove capable of insulating a finger while delivering a particular additive.

In addition, another field in which a device is required to deliver an additive or ingredient is the field of teeth or gum cleaning. Teeth cleaning is regularly required to maintain dental hygiene. Various films and residues, such as plaque, can build up on teeth and gums over a period of time, thereby adversely affecting oral health. In the past, toothbrushes have been utilized to remove such films and residues. Conventional toothbrushes typically have two ends with one end being a handle and the other containing bristles designed to disrupt and remove plaque and other residues from the surfaces being cleaned.

Although conventional toothbrushes are useful in a wide variety of environments, in some circumstances, they are less than desirable. For example, some individuals desire to maintain dental hygiene by brushing their teeth throughout the day. Unfortunately, many daily environments do not provide a setting which fosters or even allows such activity. Moreover, travelers and those working in office environments may not find it convenient to use a toothbrush during the day. For instance, toothbrushes are not generally well-suited to be carried by persons on a day-to-day basis because of their bulky shape and the need to have access to a restroom lavatory.

In response to this desire for more frequent dental hygiene and for a cleaning device that can be easily used in public, various portable toothbrushes have been developed. In particular, a number of finger-mounted teeth cleaning devices were developed that could be placed on or over a finger and wiped over the teeth and gums. These devices are typically small, portable, and disposable.

One example of such a disposable teeth cleaning device is described in U.S. Pat. No. 3,902,509 to Tundermann et al. This device is made of a high wet strength material, such as a woven or nonwoven fabric, laminated to or coated with, a water-impervious material. The water-impervious material could be a thermoplastic material, such as polypropylene. Additionally, various materials, such as flavoring materials, bacteriostats, dentrifices, or detergents could be applied to the device. To use the device, one could simply place it over a finger and rub the surface of the device over the surfaces of the teeth to remove food and plaque films.

A similar oral hygiene finger device was more recently described in U.S. Pat. No. 5,445,825 to Copelan et al. In particular, this device includes a packet of protective material that contains a membrane therein. The membrane could, for example, be made from a nonwoven cellulose fiber mat with an embossed striated texture. The device described in Copelan et al. is dry and utilizes only the moisture in a user's own mouth. This packet could also be made from foil or moisture-impervious sheet plastic material.

These teeth cleaning devices, although portable, often fail to remain tightly fitted on a user's finger during cleaning. However, some finger-mounted teeth cleaning devices were developed to contain an elastomeric material that could help prevent the device from slipping or falling off the user's finger during cleaning. Examples of such teeth cleaning devices are disclosed in U.S. Pat. Nos. 5,068,941 to Dunn; 5,348,153 to Cole; 5,524,764 to Kaufman et al.; and PCT Publication No. WO 95/31154 to Mittiga et al. Despite the apparent benefit of such elastic teeth cleaning devices, these devices remain deficient in a variety of ways. For instance, these devices are often difficult to process using high speed manufacturing techniques, thereby necessitating higher production costs. Moreover, these devices can also fail to adequately fit onto the finger of a user, can be allergenic to a user, and in some cases, lack an aesthetically pleasing appearance. In addition, these devices are often not suitable for application with various additives useful for cleaning teeth or otherwise improving oral hygiene. Furthermore, these devices are typically not breathable nor moisture-impervious.

SUMMARY OF THE INVENTION

Definitions

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes referred to as multiconstituent fibers. Fibers of this general type are discussed in, for example, U.S. Pat. Nos. 5,108,827 and 5,294,482 to Gessner. Biconstituent fibers are also discussed in the textbook *Polymer Blends and Composites* by John A. Manson and Leslie H. Sperling, copyright 1976 by Plenum Press., a division of Plenum Publishing Corporation of New York, IBSN 0-306-30831-2, at pages 273 through 277.

As used herein, the term "breathable" means pervious to water vapor and gases. In other words, "breathable barriers" and "breathable films" allow water vapor to pass therethrough, but are substantially impervious to liquid water. For example, "breathable" can refer to a film or laminate having water vapor transmission rate (WVTR) of at least about 300 g/m$^2$/24 hours measured using ASTM Standard E96-80, upright cup method, with minor variations as described in the following Test Procedure.

A measure of the breathability of a fabric is the water vapor transmission rate (WVTR) which, for sample materials, is calculated essentially in accordance with ASTM Standard E96-80 with minor variations in test procedure as set forth hereinbelow. Circular samples measuring three inches in diameter are cut from each of the test materials, and tested along with a control, which is a piece of "CELGARD" 2500 sheet from Celanese Separation Products of Charlotte, N.C. "CELGARD" 2500 sheet is a microporous polypropylene sheet. Three samples are prepared for each material. The test dish is a No. 60-1 Vapometer pan distributed by Thwing-Albert Instrument Company of Philadelphia, Pa. 100 milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 cm diameter circle having an exposed area of approximately 33.17 square centimeters. The pans are placed in a forced air oven at 100° F. (32° C.) for one hour to equilibrate. The oven is a constant temperature oven with external air circulating through it to prevent water vapor accumulation inside. A suitable forced air oven is, for example, a Blue M Power-O-Matic 600 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows: Test WVTR= (grams weight loss over 24 hours)×(315.5 g/m$^2$/24 hours).

The relative humidity within the oven is not specifically controlled. Under predetermined set conditions of 100° F. (32° C.) and ambient relative humidity, the WVTR for the "CELGARD" 2500 control has been defined to be 5000 grams per square meter for 24 hours. Accordingly, the control sample was run with each test and the preliminary test values were corrected to set conditions using the following equation: WVTR=(test WVTR/control WVTR)× (5000 g/m$^2$/24 hrs.).

As used herein, the term "conjugate fibers" refers to fibers which have been formed from at least two polymers extruded from separated extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement, wherein one polymer is surrounded by another or may be a side by side arrangement, a pie arrangement or an "islands-in-the-sea" arrangement. Conjugate fibers are taught by U.S. Pat. Nos. 5,108,820 to Kaneko et al., and 4,795,668 to Krueger et al., 5,336,552 to Strack et al. Conjugate fibers are also taught in U.S. Pat. No. 5,382,400 to Pike et al. and may be used to produced crimp in the fibers by using the differential rates of expansion and contraction of the two (or more) polymers. Crimped fibers may also be produced by mechanical means and by the process of German Patent DT 25 13 251 A1. For two component fibers, the polymers may be present in ratios of 75/25, 50/50, 25/75, or any other desired ratios. The fibers may also have shapes such as those described in U.S. Pat. Nos. 5,277,976 to Hogle et al. 5,466,410 to Hill, 5,069,970 to Largman et al., and 5,057,368 to Largman et al., which describe fibers with unconventional shapes.

As used herein, the terms "elastic" and "elastomeric" are generally used to refer to materials that, upon application of a force, are stretchable to a stretched, biased length which is at least about 125%, or one and one fourth times, its relaxed, unstretched length, and which will retract at least about 50% of its elongation upon release of the stretching, biasing force.

As used herein, the term "filament" refers to a generally continuous strand that has a large ratio of length to diameter, such as, for example, a ratio of 1000 or more.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited on a collecting surface.

As used herein, a "moisture barrier" refers to any material that is relatively impermeable to the transmission of fluids, i.e. a fabric having a moisture barrier can have a blood strikethrough ratio of 1.0 or less according to ASTM test method 22.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

As used herein, the term "nonwoven web" refers to a web having a structure of individual fibers or threads which are interlaid, but not in an identifiable manner as in a knitted fabric. Nonwoven webs or fabrics have been formed from many processes, such as, for example, meltblowing processes, spunbonding processes, and bonded carded web processes. The basis weight of nonwoven fabrics is usually expressed in ounces of material per square yard (osy) or grams per square meter (gsm) and the fibers diameters are usually expressed in microns. (Note that to convert from osy to gsm, multiply osy by 33.91).

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. Nos. 4,340,563 to Appel et al., 3,692,618 to Dorschner et al., 3,802,817 to Matsuki et al., 3,338,992 to Kinney, 3,341,394 to Kinney, 3,502,763 to Hartman, and 3,542,615 to Dobo et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen et al., which is incorporated herein by reference. Other composite elastic materials are described and disclosed in U.S. Pat. Nos. 4,789,699 to Kieffer et al., 4,781,966 to Taylor, 4,657,802 to Morman, and 4,655,760 to Morman et al., all of which are incorporated herein by reference thereto.

As used herein, the term "texturized" refers to a base web having projections from a surface of the web in the Z-direction. The projections can have a length, for instance, from about 0.1 mm to about 25 mm, particularly from about 0.1 mm to about 5 mm, and more particularly from about 0.1 mm to about 3 mm. The projections can take on many forms and can be, for instance, bristles, tufts, loop structures such as the loops used in hook and loop attachment structures, and the like.

SUMMARY

The present invention is generally directed to a finger glove that can fit over a finger. A finger glove of the present invention is generally formed from a base web material that is shaped into a glove. Further, the glove can contain a pocket for the insertion of a finger.

In accordance with the present invention, any material commonly used in the art to manufacture cloths, such as wipes, can be used as a base web. In particular, the base web of the present invention is typically made from a nonwoven web. More particularly, the base web of the present invention can be made from pulp fibers, synthetic fibers, thermomechanical pulp, or mixtures thereof such that the web has cloth-like properties. For instance, the base web can be made from various types of fibers, including meltblown, spunbond, bonded carded, bicomponent, and crimped fibers. Moreover, the base web can also include various other materials such as elastomeric components or texturized nonwoven materials. Various laminates, such as elastic and film laminates, can also be used in the base web. For instance, suitable elastic laminates can include stretch-bonded and neck-bonded laminates.

Furthermore, in accordance with the present invention, the finger glove can also include a moisture barrier that is incorporated into or applied as a layer to the base web. In general, a moisture barrier refers to any barrier, layer, or film that is relatively liquid impervious. In particular, the moisture barrier of the present invention can prevent the flow of liquid through the finger glove so that a finger inserted therein remains dry when the wipe is being used. In some embodiments, the moisture barrier can remain breathable, i.e., permeable to vapors, such that a finger within the glove is more comfortable. Examples of suitable moisture barriers can include films, fibrous materials, laminates, and the like.

In some embodiments, a finger glove of the present invention can be formed from multiple sections. These multiple sections can sometimes comprise different base web materials. For instance, in one embodiment, for example, the first section can be made from a texturized nonwoven material having an abrasive surface useful for cleaning. A second section, or backing, can be made from an elastic nonwoven material having form-fitting properties to help the glove effectively fit onto a finger.

In accordance with the present invention, various additives can also be applied, if desired, to the finger glove during manufacturing and/or by the consumer. For example, cationic materials, such as chitosan (poly-N-acetylglucosamine), chitosan salts, cationic starches, etc., can be applied to a glove of the present invention to help attract negatively charged bacteria and deleterious acidic byproducts that accumulate in plaque. Moreover, various other additives can also be applied. Examples of other suitable additives include, but are not limited to, dental agents, such as fluorides, peppermint oil, mint oil and alcohol mixtures; flavoring agents, such as xylitol; anti-microbial agents; polishing agents; hemostatic agents; surfactants; anti-ulcer components; and the like.

Additives can be applied to the wipe of the present invention in the form of an aqueous solution, non-aqueous solution (e.g., oil), lotions, creams, suspensions, gels, etc. When utilized, the aqueous solution can, for example, be coated, saturated, sprayed, or impregnated into the wipe. In some embodiments, the additives can be applied asymmetrically. Moreover, in some instances, it may be desired that the additives comprise less than about 100% by weight of the wipe, and in some embodiments, less than about 50% by weight of the wipe and particularly less than 10% by weight of the wipe.

It should be noted that any given range presented herein is intended to include any and all lesser included ranges. For example, a range of from 45–90 would also include 50–90; 45–80; 46–89 and the like. Thus, the range of 95% to 99.999% also includes, for example, the ranges of 96% to 99.1%, 96.3% to 99.7%, and 99.91 to 99.999%.

Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which:

FIG. 11 is a perspective view of a further alternative embodiment of a finger glove made in accordance with the present invention;

FIG. 12 is a perspective view of another alternative embodiment of a finger glove made in accordance with the present invention which is adapted to be placed over two fingers;

Figure 1:
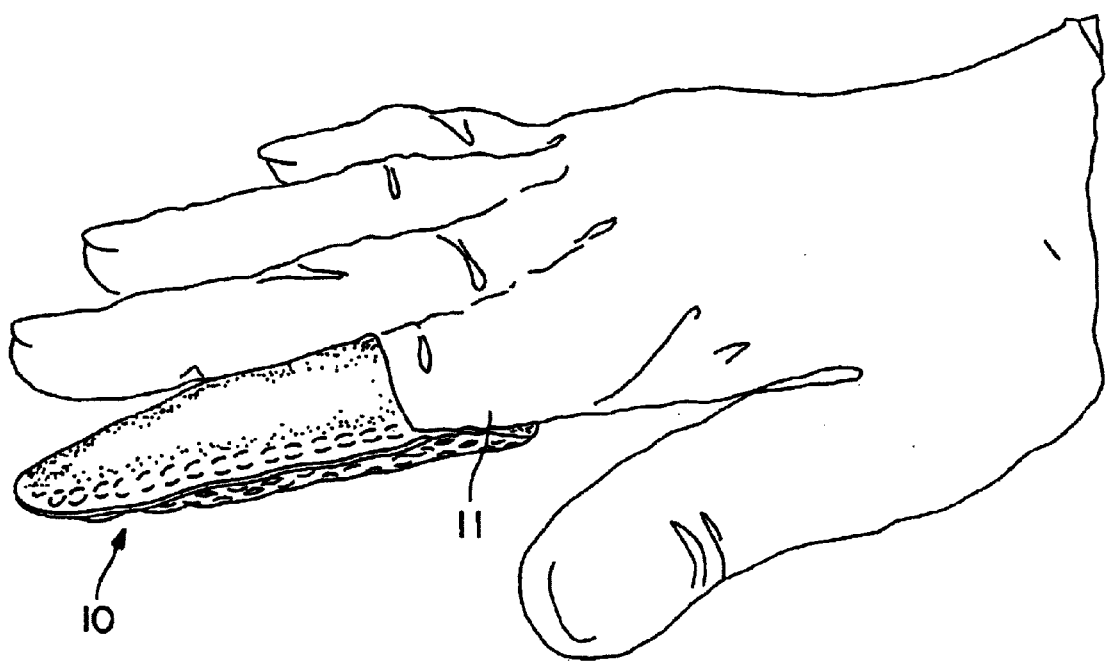
FIG. 1 is a perspective view of a finger glove on a finger according to one embodiment of the present invention.

Repeat use of reference characters in the present specification and drawings is intended to represent the same or analogous features or elements of the invention.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description.

Finger gloves made in accordance with the present invention are generally constructed from disposable materials, such as nonwoven webs made from synthetic and/or pulp fibers. For example, when used as an oral cleaning device, the finger glove typically includes a texturized surface adapted to scrub or brush the teeth or gums of a user. Further, the finger glove can also include an elastic component for providing the glove with form-fitting properties.

For instance, it has been discovered that by forming a finger glove with an elastic nonwoven material in accordance with the present invention, the resulting glove can snugly fit onto a person's finger so that the glove can more effectively remain on the finger throughout use. Moreover, a finger glove of the present invention can remain "breathable" to aid in a person's comfort during use, while also remaining capable of substantially inhibiting the transfer of liquids from the outer surface of the glove to the person's finger. The transfer of liquids can be controlled using a liquid-impervious material and/or by using a highly liquid absorbent material.

A finger glove of the present invention can generally be formed in a variety of ways. For instance, in one embodiment, the finger glove can be formed as a unitary structure from a particular base web material, such as an elastomeric nonwoven base web material. Moreover, in another embodiment of the present invention, the finger glove can be formed from two or more sections of base web material. Each section can be identical or different, depending on the desired characteristics of the finger glove. For example, in one embodiment, the finger glove is formed from two sections, wherein one section is formed from a textured nonwoven material and the other section is formed from an elastomeric nonwoven material.

Referring to FIGS. 1–9, various embodiments of finger gloves made in accordance with the present invention are depicted. In general, a finger glove of the present invention can be used to apply medications, ointments, for make-up removal etc. For example, in one embodiment, as shown in FIG. 1, a finger glove 10 can be placed over a finger 11 for cleaning the oral cavity of a person.

Figure 8:
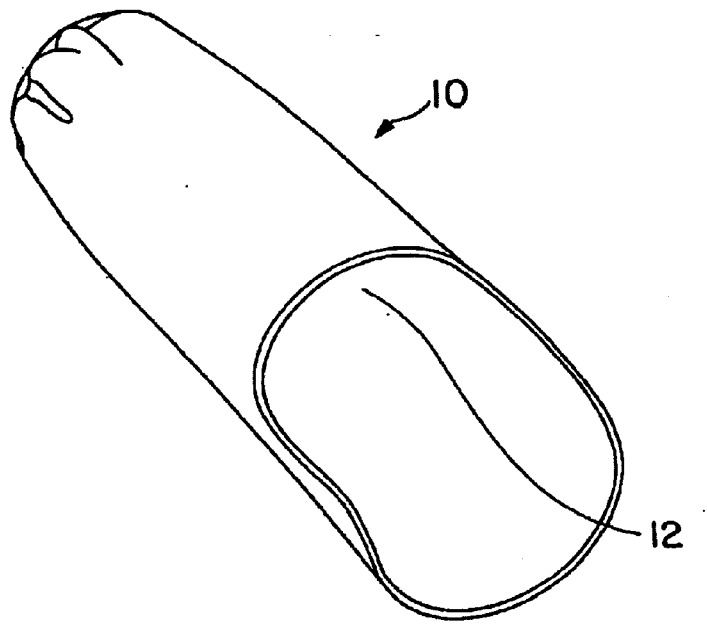
FIG. 8 is a perspective view of an embodiment of a finger glove having a unitary structure.

One embodiment of a finger glove of the present invention is depicted in FIG. 8. As shown, the finger glove 10 is formed as a unitary structure from a single piece of fabric.

Figure 2:
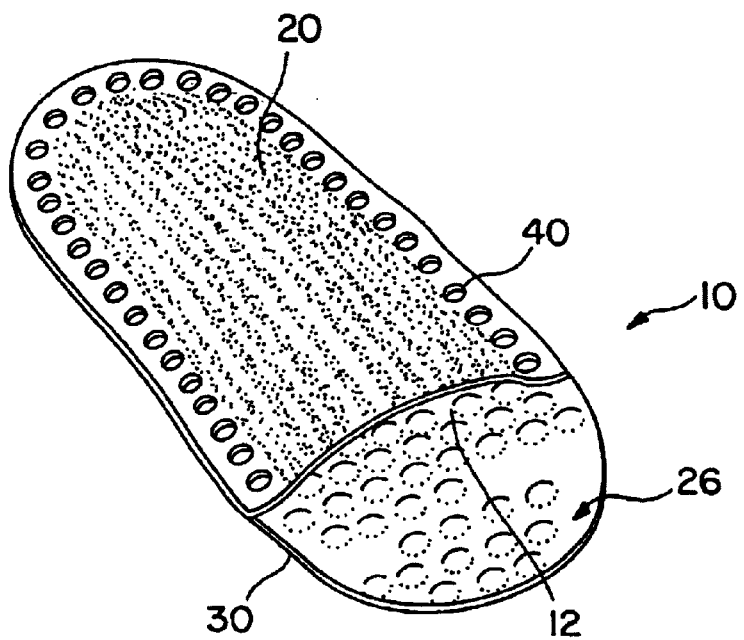
FIG. 2 is a perspective view of a two-sided finger glove according to one embodiment of the present invention.
Figure 3:
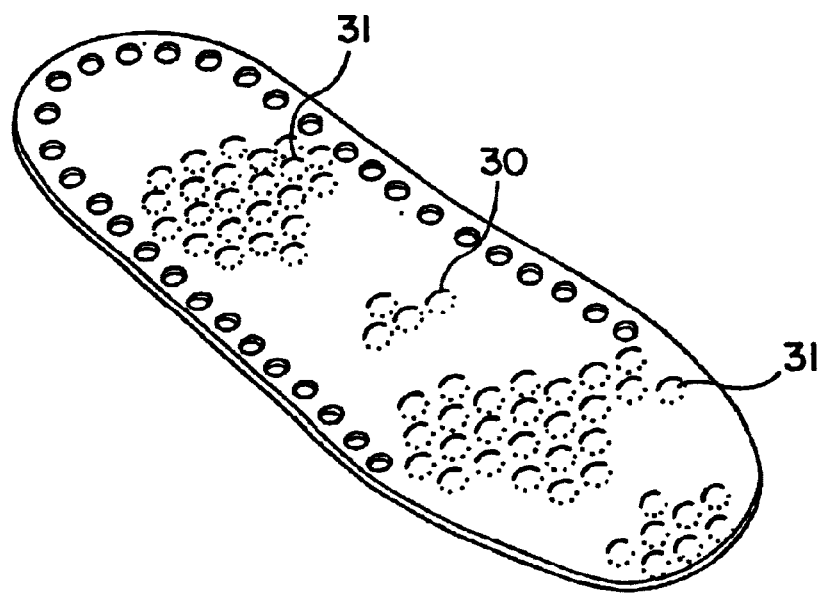
FIG. 3 is a perspective view of a bottom section of a two-sided finger glove according to one embodiment of the present invention.
Figure 4:
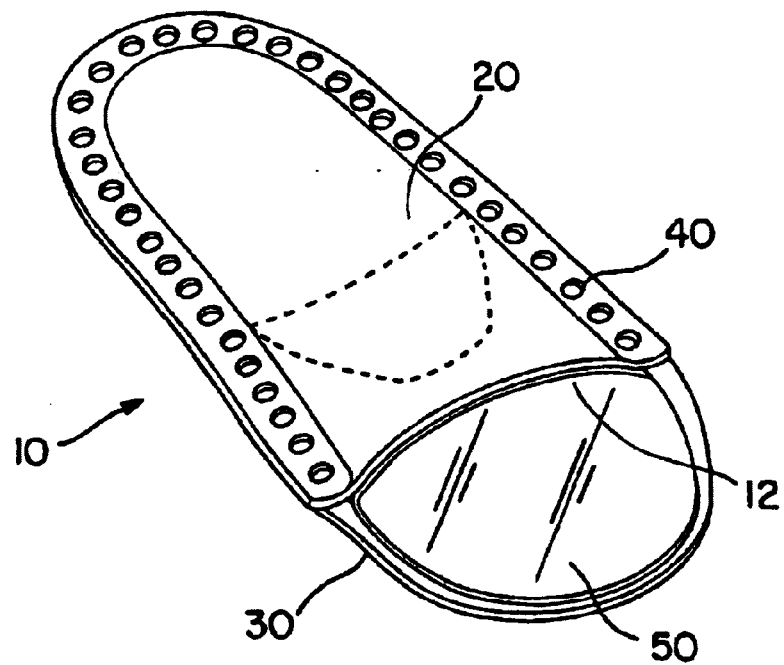
FIG. 4 is a perspective view of the bottom section of the two-sided finger glove of FIG. 3 attached to a top section to form the two-sided finger glove according to one embodiment of the present invention.

Referring to FIGS. 2–4, another embodiment of a finger glove of the present invention is depicted. As shown, instead of a unitary structure, the finger glove 10 is made from a first section 20 and a second section 30. Generally, one section of the finger glove 10 can be bonded or attached to the other section in a finger-shaped pattern by any manner known in the art, such as by adhesive, thermal, or mechanical bonding, so that the connection of the sections can form a pocket 12 for the insertion of a finger. In the embodiment depicted in FIG. 2, for example, the first section 20 is attached in a finger-shaped pattern to the second section 30 at their respective outer edges via the seams 40 to form a finger glove 10 having a pocket 12. Once each section is bonded or attached at the seams 40, the materials forming each of the sections 20 and 30 can then be cut adjacent to the seams such that the finger-shaped glove 10 is formed.

In one embodiment of the present invention, in order to soften the feel of the seams of the finger glove during use, a plurality of cuts can be made along the edges of the seam. The cuts, which can be referred to as microcuts, can be narrowly spaced along the seam. The cuts can be, for instance, less than 1 cm apart, particularly less than about 0.5 cm apart, and more particularly, less than about 1 mm apart. The cuts can extend substantially the entire width of the seam. For instance, the length of the cuts can be from about 0.1 cm to about 0.5 in length depending upon the particular application.

The microcuts can be formed into the seam using any suitable process. For instance, the cuts can be made using cutting dyes, laser technology, ultrasonic knives, and the like.

Figure 5:
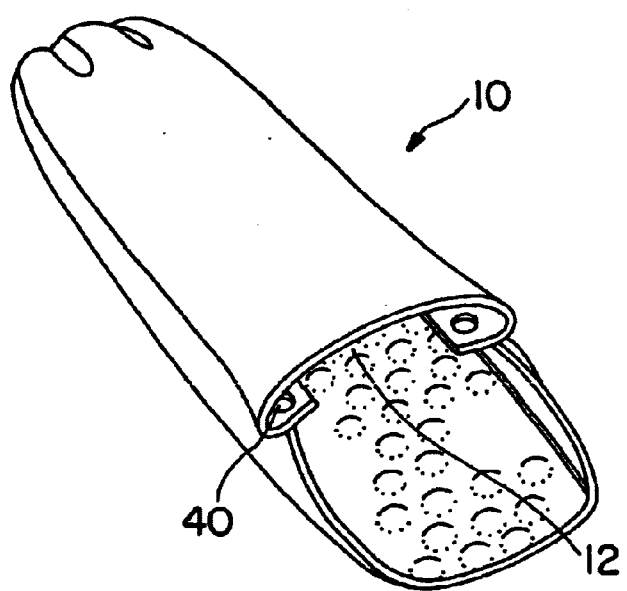
FIG. 5 is a perspective view of a finger glove turned "inside-out" according to one embodiment of the present invention.
Figure 6:
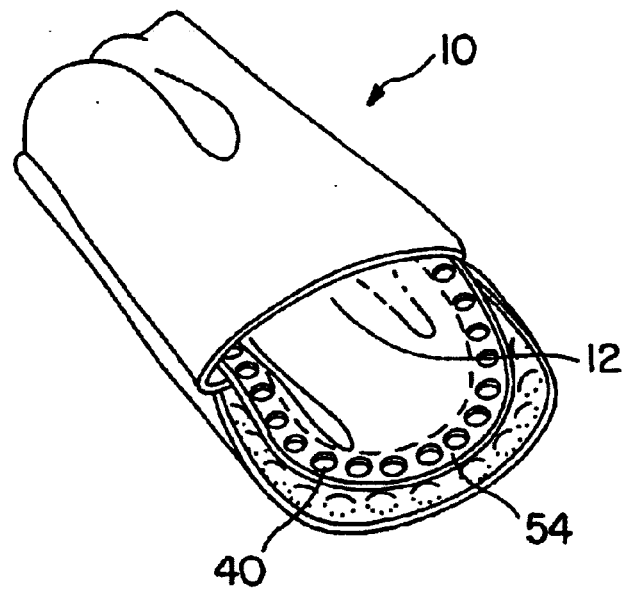
FIG. 6 is a perspective view of a finger glove turned "inside-out" according to another embodiment of the present invention.

In some embodiments, as depicted in FIGS. 5–6, the finger glove 10 can also be turned inside-out such that the seams 40 are located inside the pocket 12. For example, as shown in FIG. 6, the seams 40 of the finger glove 10 can be pushed into the pocket 12 such that the seams 40 remain on the inside of the glove 10, as depicted in FIG. 5. This "inside-out" position, as shown in FIG. 5, can provide the finger glove with improved aesthetics. Moreover, the seams in the inside-out position can also provide a better fit by providing more friction applied to the finger. In addition, in some embodiments, this "inside-out" position can enable the glove 10 to be more resistant to "flattening out" during use. Further, inverting the finger glove can prevent the seams from causing irritation in the mouth when used.

Figure 10:
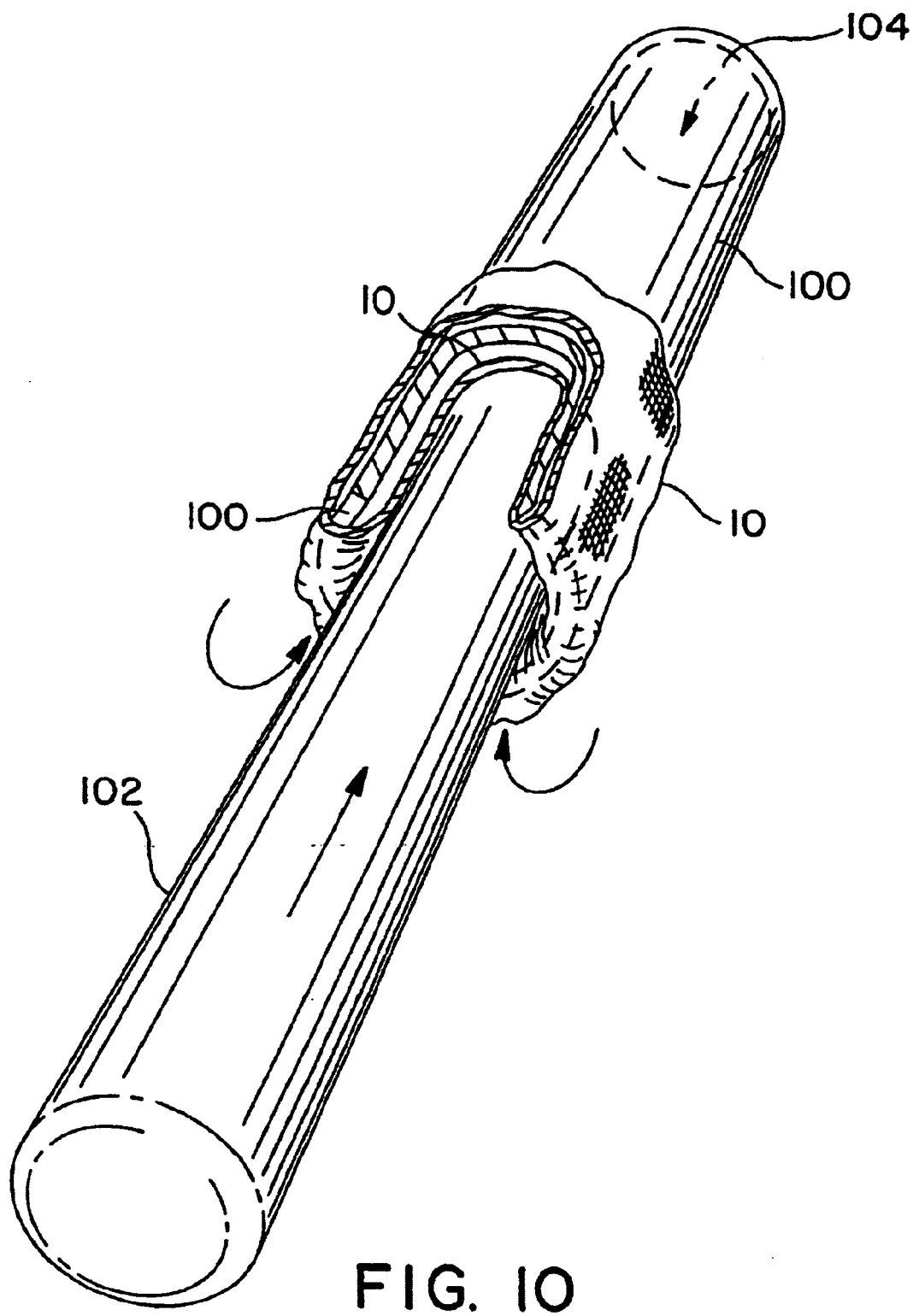
FIG. 10 is a perspective view with cut away portions illustrating one embodiment of a method for turning a finger glove of the present invention inside-out.

Various methods can be used in order to place the finger glove in the inside-out position. For instance, the finger glove can be turned inside-out using a pressurized gas, a vacuum, or mechanical means. For example, one mechanical method for inverting the finger glove is illustrated in FIG. 10. As shown, in this embodiment, the finger glove 10 is placed over a cylinder 100. The cylinder 100 defines a passage 104. In order to invert the finger glove 10, a rod 102, preferably with a compressible tip, is used to push against the closed end of the finger glove until the finger glove is pushed all the way through the passage 104. Through this process, the finger glove 10 is inverted.

As shown in FIGS. 1–4, the first section 20 can, in some embodiments, have a length greater than the second section 30 such that first section 20 includes a portion (or pull-on tab) 26 that extends beyond the edge of the second section 30. By extending beyond the second section 30, the portion 26 can facilitate placement of a finger glove 10 over a finger. In particular, a user can conveniently grab the portion 26 to place the finger glove 10 over a finger. Besides the first section 20, a pull-on tab can be positioned on any suitable portion of the finger glove. For instance, the pull-on tab can be located on the second section also.

Further, in another embodiment, the pull-on tab 26 can also be provided in the middle portion of the finger glove 10 such that a user can the pull the tab 26 in a direction perpendicular to the lengthwise direction of a flattened finger glove. As a result, the tab 26 can facilitate the insertion of a finger into the glove 10 by "spreading out" the glove in an upwardly direction as a finger is inserted therein.

Figure 9:
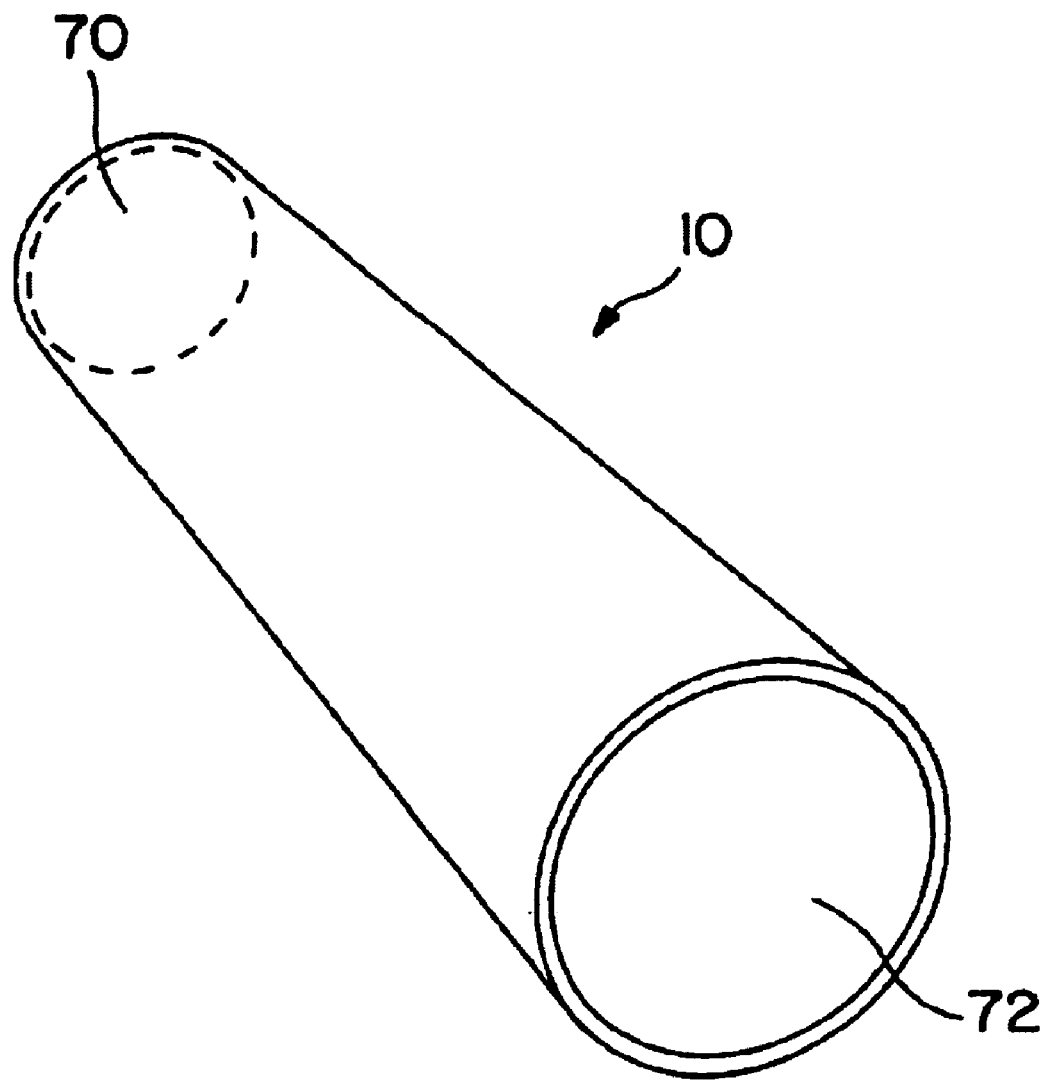
FIG. 9 is a perspective view of a tapered finger glove having two open ends according to one embodiment of the present invention.

Moreover, although not specifically shown, a finger glove of the present invention can include bristles on the first section 20 and/or 9, the second section 30, particularly when used as an oral cleaning device. For example, bristles such as described in U.S. Pat. Nos. 4,617,694 to Bori or 5,287,584 to Skinner, which are incorporated herein by reference, can be utilized. Further, in other embodiments, as shown in FIG. 9, a finger glove 10 can also be provided with a tapered shape to enhance the ability of the glove to fit onto a finger. In addition, as shown in FIG. 9, a glove 10 can have two open ends 70 & 72 so that a finger can be inserted completely therethrough.

In some embodiments of the present invention, it may also be desirable to provide the finger glove 10 with an additional fastening means. In addition to or alternative to an elastic component, the dental wipe can include a fastening mechanism which can attach to one finger of a user, while the finger glove is fitted onto another finger. For example, as shown in FIG. 7, one embodiment of a fastening mechanism of the present invention includes a fastening portion 60 that can fit around a finger of a user.

Figure 7:
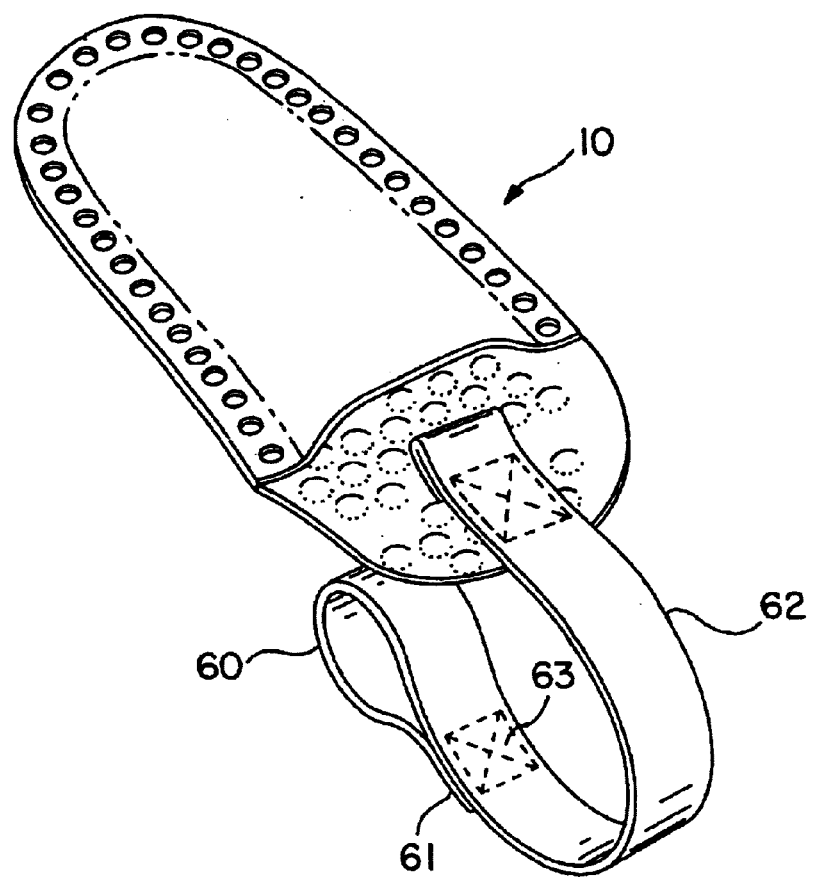
FIG. 7 is a perspective view of a finger glove having a fastening mechanism according to one embodiment of the present invention.

In one embodiment of the present invention, as shown in FIG. 7, the fastening mechanism can also include a linking portion 62 for attaching the fastening portion 60 to the finger glove 10. When utilized, the linking portion 62 can be attached to the glove using a variety of well known attachment methods, such as thermal, chemical, or mechanical bonding. For example, in one embodiment, the linking portion 62 is attached to a finger glove 10 by an adhesive. In another embodiment, the linking portion 62 is attached to a glove 10 by stitching.

In general, the linking portion 62 can be made from a variety of materials, such as strings, bands, cords, fibers, nonwovens, etc. For most applications, the linking portion 62 can have a length of from about 1 inch to about 12 inches.

In general, the fastening portion 60 can have any shape as long the shaped fastening portion can fit on the finger. For instance, in the embodiment shown in FIG. 7, a fastening portion 60 is formed to have a loop or ring shape so that it can be secured on a finger. Moreover, the fastening portion can also be formed into a certain shape from the linking portion itself. For instance, as shown in FIG. 7, an end 61 of a linking portion 62 is folded and attached to the portion 63 of the linking portion 62 via stitching to form a ring-shaped fastening portion 60. It should be understood that the end 61 can also be attached to a portion 63 by any attachment method known in the art, such as, for example, thermal, chemical, or mechanical bonding methods. Although not specifically depicted, the fastening portion 60 can also be formed from a material separate from the linking portion 62. When formed separately, the fastening portion 60 can be attached to linking the portion 60 by any attachment method known in the art, such as, for example, thermal, chemical, or mechanical bonding methods.

Typically, the fastening portion can be made from the same or a different material than the linking portion. For example, in one embodiment, a fastening portion 60 contains an elastic material, such as an elastomeric nonwoven, which can allow the fastening portion to fit more tightly around a finger.

In general, the finger glove of the present invention, such as depicted in FIGS. 1–9, can be formed from a variety of materials. For instance, in one embodiment, the first section 20 and the second section 30 are formed from a base web. It should be understood, however, that, as used herein, a base web of the present invention is meant to include one or more layers of fibrous materials. Generally, a finger glove made according to the present invention can be made from any material used in the art for making wipes.

For most applications, finger gloves made in accordance with the present invention are constructed from nonwoven webs containing an elastic component referred to herein as an "elastic nonwoven." An elastic nonwoven is a nonwoven material having non-elastic and elastic components or having purely elastic components.

The elastic component, for instance, can form a separate section of the finger glove. For example, the finger glove can be made from two or more sections of material that includes a first section made from a non-elastic material and a second section made from an elastic material. In one embodiment, the non-elastic material can be used to brush the teeth, gums and tongue of the user, while the elastic material can be used to ensure that the finger glove fits snugly over the finger of the user. In one embodiment, the non-elastic material can be texturized for brushing the teeth, gums and tongue, while the elastic material can have a smooth surface for use in polishing the teeth, gums and tongue of the user.

Alternatively, the finger glove can be made from a single piece of material that contains an elastic component. For example, in this embodiment, the elastic component can be a film, strands, nonwoven webs, or elastic filament incorporated into a laminate structure that is well suited to brushing or scrubbing one's teeth. Non-elastic materials used in the present invention typically include nonwoven webs or films. The nonwoven webs, for instance, can be melt-blown webs, spunbond webs, carded webs, and the like. The webs can be made from various fibers, such as synthetic or natural fibers.

For instance, in one embodiment, synthetic fibers, such as fibers made from thermoplastic polymers, can be used to construct the finger glove of the present invention. For example, suitable fibers could include melt-spun filaments, staple fibers, melt-spun multi-component filaments, and the like.

These synthetic fibers or filaments used in making the nonwoven material of the base web may have any suitable morphology and may include hollow or solid, straight or crimped, single component, conjugate or biconstituent fibers or filaments, and blends or mixtures of such fibers and/or filaments, as are well known in the art.

The synthetic fibers used in the present invention may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof. As used herein, the term "blend" means a mixture of two or more polymers. Furthermore, unless otherwise specifically limited, the term "polymer" shall include all possible geometrical configurations of the molecule. These configurations include, but are not limited to, isotactic, synditactic, and random symmetries.

Exemplary thermoplastics include, without limitation, poly(vinyl) chlorides, polyesters, polyamides, polyfluorocarbons, polyolefins, polyurethanes, polystyrenes, poly(vinyl) alcohols, caprolactams, and copolymers of the foregoing, and elastomeric polymers such as elastic polyolefins, copolyether esters, polyamide polyether block copolymers, ethylene vinyl acetates (EVA), block copolymers having the general formula A-B-A' or A-B like copoly (styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene), A-B-A-B tetrablock copolymers and the like.

Many polyolefins are available for fiber production, for example polyethylenes such as Dow Chemical's PE XU 61800.41 linear low density polyethylene ("LLDPE") and 25355 and 12350 high density polyethylene ("HDPE") are such suitable polymers. Fiber-forming polypropylenes include Exxon Chemical Company's Escorene® PD 3445 polypropylene and Montell Chemical Co.'s PF-304 and PF-015. Many other polyolefins are commercially available and include polybutylenes and others.

Examples of polyamides and their methods of synthesis may be found in "Polymer Resins" by Don E. Floyd (Library of Congress Catalog No. 66-20811, Reinhold Publishing, New York, 1966). Particularly commercially useful polyamides are nylon-6, nylon 6,6, nylon-11 and nylon-12. These polyamides are available from a number of sources such as Emser Industries of Sumter, S.C. (Grilon® & Grilamid® nylons), Atochem Inc. Polymers Division of Glen Rock, N.J. (Rilsan® nylons), Nyltech of Manchester, N.H. (grade 2169, Nylon 6), and Custom Resins of Henderson, Ky. (Nylene 401-D), among others.

As stated above, synthetic fibers added to the base web can also include staple fibers which can be added to increase the strength, bulk, softness and smoothness of the base sheet. Staple fibers can include, for instance, various polyolefin fibers, polyester fibers, nylon fibers, polyvinyl acetate fibers, cotton fibers, rayon fibers, non-woody plant fibers, and mixtures thereof. In general, staple fibers are typically longer than pulp fibers. Staple fibers can increase the strength and softness of the final product.

The fibers used in a base web of the present invention could also be curled or crimped. The fibers can be curled or crimped, for instance, by adding a chemical agent to the fibers or subjecting the fibers to a mechanical process. Curled or crimped fibers may create more entanglement and void volume within the web and further increase the amount of fibers oriented in the z-direction as well as increase web strength properties. As used herein, the z-direction refers to the direction perpendicular to the length and width of the base web.

The synthetic fibers added to the base web can also include bicomponent fibers. Bicomponent fibers are fibers that can contain two materials such as but not limited to in a side by side arrangement in a matrix-fibril arrangement wherein a core polymer has a complex cross-sectional shape, or in a core and sheath arrangement. In a core and sheath fiber, generally the sheath polymer has a lower melting temperature than the core polymer to facilitate thermal bonding of the fibers. For instance, the core polymer, in one embodiment, can be nylon or a polyester, while the sheath polymer can be a polyolefin such as polyethylene or polypropylene. Such commercially available bicomponent fibers include "CELBOND" fibers marketed by the Hoechst Celanese Company.

Besides or in addition to synthetic fibers, pulp fibers can also be used to construct the finger glove of the present invention. The pulp fibers used in forming the base web may be soft wood fibers having an average fiber length of greater than 1 mm, and particularly from about 2 to 5 mm based on a length weighted average. Such fibers can include northern softwood kraft fibers, redwood fibers, and pine fibers. Secondary fibers obtained from recycled materials may also be used. In addition, hardwood pulp fibers, such as eucalyptus fibers, can also be utilized in the present invention.

Besides the above-mentioned fibers, thermomechanical pulp fibers can also be added to the base web. Thermomechanical pulp, as is known to one skilled in the art, refers to pulp that is typically cooked during the pulping process to a lesser extent than conventional pulps. Thermomechanical pulp tends to contain stiff fibers and has higher levels of lignin. Thermomechanical pulp can be added to the base web of the present invention in order to create an open pore structure, thus increasing bulk and absorbency and improving resistance to wet collapse.

When present, thermomechanical pulp can be added to a layer of the base web in an amount from about 10% to about 30% by weight of the fibers. When using thermomechanical pulp, a wetting agent is also preferably added during formation of the web. The wetting agent can be added in an amount less than about 1% by weight of the fibers and, in one embodiment, can be a sulphonated glycol.

When pulp fibers are used to form the base web, the web can also be treated with a chemical debonding agent to reduce inner fiber-to-fiber strength. Suitable debonding agents that may be used in the present invention when the base web contains pulp fibers include cationic debonding agents such as fatty dialkyl quaternary amine salts, mono fatty alkyl tertiary amine salts, primary amine salts, imidazoline quaternary salts, and unsaturated fatty alkyl amine salts. Other suitable debonding agents are disclosed in U.S. Pat. No. 5,529,665 to Kaun, which is incorporated herein by reference. In one embodiment, the debonding agent can be an organic quaternary ammonium chloride. In this embodiment, the debonding agent can be added to the fiber furnish in an amount from about 0.1% to about 1% by weight, based on the total weight of fibers present within the furnish.

Moreover, in some embodiments of the present invention, a base web of the present invention can also be hydraulically entangled (or hydroentangled) to provide further strength. Hydroentangled webs, which are also known as spunlace webs, refer to webs that have been subjected to columnar jets of a fluid that cause the fibers in the web to entangle. Hydroentangling a web typically increases the strength of the web. Thus, according to the present invention, in order to increase the strength of a web, the base web of the present invention can be hydroentangled. For example, in one embodiment, the base web can comprise HYDROKNIT®, a nonwoven composite fabric that contains 70% by weight pulp fibers that are hydraulically entangled into a continuous filament material. HYDROKNIT® material is commercially available from Kimberly-Clark Corporation of Neenah, Wisconsin. Hydraulic entangling may be accomplished utilizing conventional hydraulic entangling equipment such as may be found in, for example, in U.S. Pat. Nos. 3,485,706 to Evans or 5,389,202 to Everhart et al., the disclosures of which are hereby incorporated by reference.

As mentioned above, for most applications, nonwoven webs used to construct a finger glove will contain synthetic fibers. For nonwoven webs containing substantial amounts of synthetic fibers, the webs may be bonded or otherwise consolidated in order to improve the strength of the web. Various methods may be utilized in bonding webs of the present invention. Such methods include through air bonding and thermal point bonding as described in U.S. Pat. No. 3,855,046 to Hansen, et al. which is incorporated herein by reference. In addition, other conventional means of bonding, such as oven bonding, ultrasonic bonding, hydroentangling, or combinations of such techniques, may be utilized in certain instances.

In one embodiment, thermal point bonding is used which bonds the fibers together according to a pattern. In general, the bonding areas for thermal point bonding, whether pattern unbonded or pattern bonded fabrics, can be in the range of 50% total bond area or less. More specifically, the bond areas of the present inventive webs can be in the range of about 40% total bond area or less. Even more specifically, the bond areas can be in the range of about 30% total bond area or less and may be in the range of about 15% total bond area or less. Typically, a bond area of at least about 10% can be acceptable for creating the base webs of the present invention, although other total bond areas will fall within the scope of the invention, depending on the particular characteristics desired in the final product. Stated generally, the lower limit on the percent bond area suitable for forming the nonwoven material of the present invention is the point at which fiber pull-out excessively reduces the surface integrity and durability of the material. The percent bond areas will be affected by a number of factors, including the type(s) of polymeric materials used in forming the fibers or filaments of the nonwoven web, whether the nonwoven web is a single- or multi-layer fibrous structure, and the like. Bond areas ranging from about 15% to about 50%, and more particularly from about 15% to about 40%, have been found suitable.

Base webs constructed for use in the finger glove the present invention desirably include a texturized surface where the finger glove is to contact a user's teeth and gums. The texturized surface can facilitate removal of residue and film from the teeth and gums. The texturized surface can be positioned on the finger glove only where the finger glove is to contact the teeth and gums or can completely cover the exterior surface of the finger glove. In this regard, referring to FIG. 3, one embodiment of the present invention includes a second section 30 that is made from a base web comprising a nonwoven texturized material. When a second section 30 is made from such a nonwoven texturized material, the finger glove 10 can more effectively clean teeth or gums. In particular, when the finger glove 10 is placed onto a finger, as shown in FIG. 1, the second section 30 can be used in order to brush the teeth or gums of the desired subject.

The manner in which a texturized surface is formed on a nonwoven web for use in the present invention can vary depending upon the particular application of the desired result. In the embodiment shown in FIG. 3, the second section 30 is made from a nonwoven web that has been thermally point unbonded to form a plurality of tufts 31. As used herein, a substrate that has been "thermally point unbonded" refers to a substrate that includes raised unbonded areas or lightly bonded areas that are surrounded by bonded regions. For example, as shown in FIG. 3, the tufts 31 are the unbonded or lightly bonded areas that form raised projections off the surface of the nonwoven web to provide the necessary texture.

It is believed that the thermally point unbonded abrasive surfaces made according to the present invention are unique and provide various advantages and benefits not only when used in finger glove applications, but also when used in other applications. For instance, referring to FIG. 14, a point unbonded material generally 76 made according to the present invention is shown. Besides being used to construct finger gloves, it is believed that this material can also be used as an abrasive material in various applications, including use in sanding or polishing products, washcloths, brushes, etc. Such materials are defined by having semi-rigid protuberances of a certain height, particularly having a height of greater than about 0.02 inches.

Figure 14:
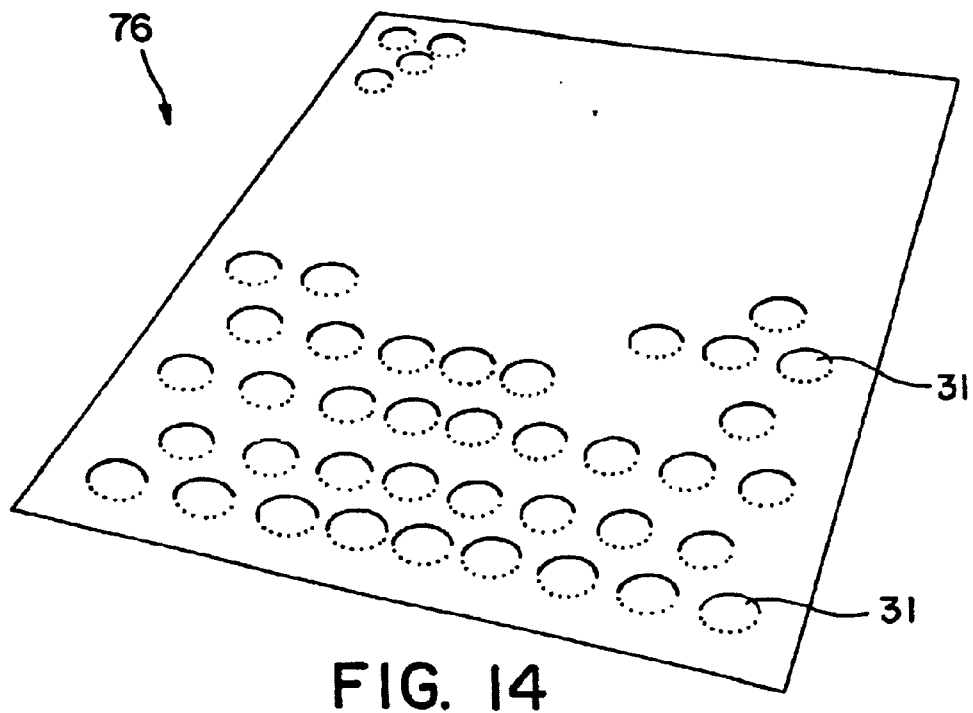
FIG. 14 is a perspective view of a texturized material for use in the present invention.

In the past, various point unbonded products have been made. For instance, a point unbonded material is commonly used as the loop material for a hook and loop fastener. Materials made in the past, however, have not been made with protuberances or tufts 31 as shown in FIG. 14 with the height of the present invention. The present inventors have discovered not only a new process for producing point unbonded materials, but also a new product having improved abrasive properties.

Figure 15:
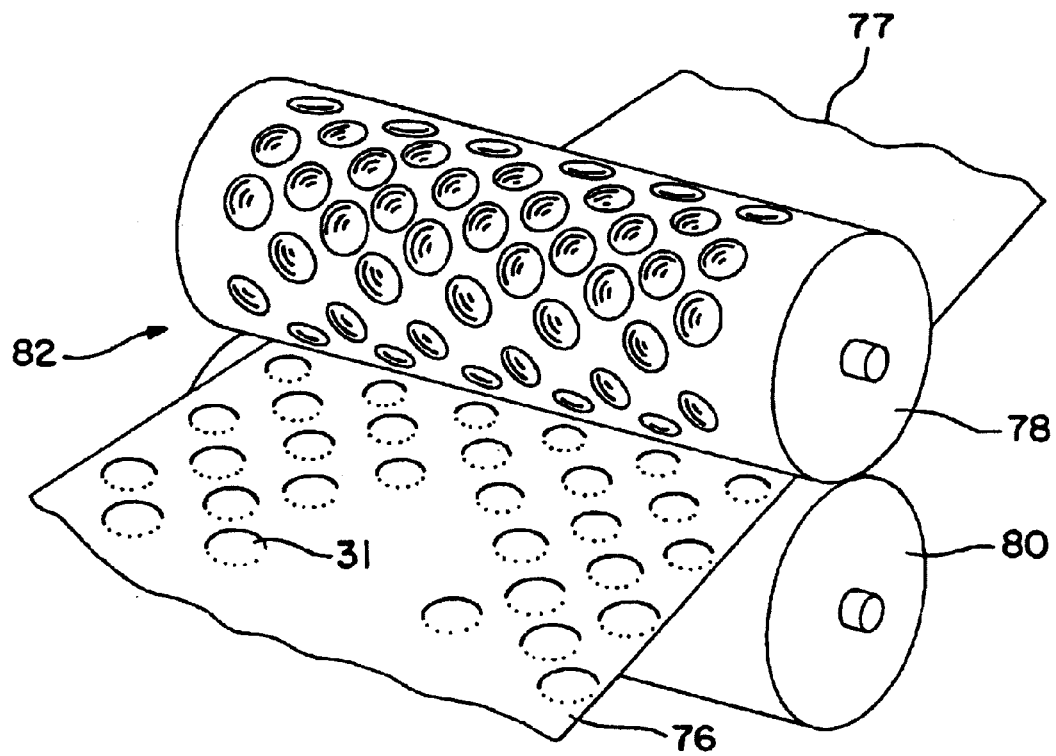
FIG. 15 is a perspective view of one embodiment of a process for producing the material illustrated in FIG. 14.

Referring to FIG. 15, one embodiment of a process for producing the point unbonded material 76 is illustrated. As shown, a nonwoven substrate 77 is fed into a nip generally 82 formed between a first patterned roll 78 and a second smooth roll 80. Once the substrate is fed through the nip 82, the tufts 31 are formed. As shown, the tufts 31 are surrounded by bonded, compressed regions.

The substrate 77 used to product the point unbonded material 76 can vary depending upon the particular application. For instance, the substrate 77 can be a single layer or can include multiple layers of material. For most applications, the total basis weight of the substrate 77 should be at least 3 osy, and particularly from about 3 osy to about 9 osy. Higher basis weights are needed in order to produce tufts 31 with an appropriate height.

For most applications, the substrate 77 should also include at least one nonwoven layer that has a high bulk to mass ratio. Examples of materials having high bulk include through air bonded nonwoven webs made from polymeric fibers and filaments. The nonwoven webs can be made from crimped polymeric fibers and filaments and/or from fibers and filaments having a shaped cross-sectional profile. For example, crimped bicomponent polyethylene/polypropylene fibers can be used. Shaped fibers include pentalobal fibers and hollow fibers.

Besides nonwovens having high bulk, the substrate 77 can also include films. For example, in one embodiment, a nonwoven web can be combined with a moisture barrier film in producing the point unbonded material 76.

As shown in FIG. 15, once the appropriate susbstrate 77 is chosen, the substrate is fed through the nip 82. In one embodiment, the point unbonded material 76 is formed through a thermal bonding process. For instance, in one embodiment, the pattern roll 78 and/or the smooth roll 80 can be heated to a temperature sufficient to melt and fuse the substrate 77 in the areas between the tufts 31. The temperature to which the rolls 78 and 80 are heated depends upon the particular application, and particularly on the materials that are used to form the substrate 77. The temperature to which the rolls is heated to also dependent upon the amount of pressure applied to the substrate 77.

In one embodiment, when processing substrates containing polyolefin fibers, the rolls can be heated to a temperature of from about 230° F. to about 280° F., and particularly from about 240° F. to about 260° F. For most most applications, both rolls 78 and 80 are heated. Patterned roll 78, however, can be heated to a higher temperature than roll 80 and vice versus.

When producing the point unbonded material 76, the speed of the substrate entering the nip, the amount of tension placed upon the substrate and the pressure within the nip are all important factors that need to be optimized in producing the product. For instance, the speed at which the substrate is fed through the nip 82 can vary from about 5 feet per minute to about 100 feet per minute when using conventionally sized rolls.

Besides thermal bonding, ultrasonic bonding can also be used to produce the point unbonded material 76. Ultrasonic bonding can be carried out using a stationary device (not shown) or a rotary device as shown in FIG. 15. During ultrasonic bonding, patterned roll 78 is vibrated which causes the tufts 31 to form. The present inventors have determined that ultrasonic bonding operates more efficiently than thermal bonding. It has also been determined that ultrasonic bonding is capable of processing thicker and heavier substrates than thermal bonding. For example, ultrasonic bonding can process substrates having a basis weight up to 9 osy. Conventional thermal bonding systems, however, are better suited for processing substrates having a basis weight up to about 5 osy. Ultrasonic bonding also produces subtle differences in the morphological characteristics of the surface in comparison to conventional thermal bonding.

As described above, the point unbonded material 76 contains tufts having a height of at least 0.02 inches. More particularly, the height of the tufts will vary from about 0.05 inches to about 0.1 inches. As shown in FIG. 15, the tufts can have a circular shape. It should be understood, however, that tufts 31 can have any suitable shape. For instance, the tufts can be square, triangular, or even in the shpe of a doughnut.

The total bond area surrounding the tufts 31 can also vary depending upon the particular application. For most embodiments, the bond area surrounding the tufts can be from about 15% to about 40% of the surface area of the material, and particularly from about 20% to about 40% of the surface area of the material.

In one particular embodiment of the present invention, the point unbonded material 76 is made from two substrate layers. The first substrate layer is a through air bonded web having a basis weight of 3.25 osy. The web can be made from crimped bicomponent polypropylene/polyethylene fibers. The second substrate, on the other hand, is a through air bonded nonwoven web made from shaped pentalobal fibers. The second web can also have a basis weight of about 3.25 osy. Both webs can be fed simultaneously into the nip 82 and subjected to ultrasonic bonding to produce tufts 31.

In another alternative embodiment of the present invention, the point unbonded material 76 is made from a breathable stretched polyethylene film sandwiched between a through air bonded nonwoven web having a basis weight of about 3.5 osy and a spunbound web having a basis weight of 0.5 osy. The first nonwoven web can be made from crimped bicomponent fibers, while the spunbond web can be made from polypropylene filaments.

It should be understood, however, that the materials and conditions used to make the point unbonded material 76 can vary depending upon the ultimate application of the material.

Besides point unbonded materials, there are many other methods for creating texturized surfaces on base webs and many other texturized materials can be utilized.

Examples of known nonwoven, texturized materials, include rush transfer materials, flocked materials, wireform nonwovens, and the like. Moreover, through-air bonded fibers, such as through-air bonded bicomponent spunbond, or point unbonded materials, such as point unbonded spunbond fibers, can be incorporated into the base web to provide texture to the wipe.

Textured webs having projections from about 0.1 mm to about 25 mm, such as pinform meltblown or wireform meltblown, can also be utilized in a base web of the present invention. Still another example of suitable materials for a texturized base web include textured coform materials. In general, "coform" means a process in which at least one meltblown diehead is arranged near a chute through which other materials are added to the web while it forms. Such other materials can include, for example, pulp, superabsorbent particles, or cellulose or staple fibers. Coform processes are described in U.S. Pat. Nos. 4,818,464 to Lau and 4,100,324 to Anderson et al. Webs produced by the coform process are generally referred to as coform materials.

In one embodiment, the texturized material can be a loop material. As used herein, a loop material refers to a material that has a surface that is at least partially covered by looped bristles. It is believed that looped bristles provide various advantages in relation to conventional bristles. For example, the inherent stiffness in a looped structure allows the use of finer yarns and a corresponding increase in surface area for a given stiffness. The lack of a sharp end on a looped bristle may reduce abrasion, which refers to the damage that can occur to soft tissue in the mouth.

The looped bristles that can be used in the present invention can vary depending upon the particular application. For instance, the stiffness of the looped bristles can be varied by varying different factors, including the height of the loop, the inherent properties of the looped material, the fiber diameter, the fiber type, and any post-formation treatments (e.g. chemical coatings) that may be performed on the looped material.

In general, the height of the looped bristles should be short enough so that the loops are unlikely to get snagged on teeth or other structures being scrubbed, but still sufficiently long to be effective in cleaning interproximal areas. For most applications, the loops should be less than about 20 mm, particularly from about 1 mm to about 5 mm, and more particularly from about 1.5 mm to about 3.5 mm. The height of the looped bristles on a loop material can be homogenous or heterogeneous. The looped bristles can be contained on the looped material according to a particular pattern or can be randomly arranged on the loop material. For example, in one embodiment, the looped bristles can be arranged in rows and columns on the loop material. The looped bristles can be arranged vertically or at any suitable angle to the surface of the material. Further, the looped bristles can be sparsely spaced apart or can be densely packed together.

The loop material can be made in a number of different ways. For example, the loop can be a woven fabric or a knitted fabric. In one embodiment, the loop material is made by needle-punching loops into a substrate. In other embodiments, the loop material can be formed through a hydroentangling process or can be molded, such as through an injection molding process. Of course, any other suitable technique known in the art for producing looped bristles can also be used.

The looped bristles can be made from various natural or synthetic materials. For instance, the bristles can be made from polyester, nylon, polypropylene, polyethylene, polylactic acid, or various other polymers. The looped bristles can also be made from natural fibers, including cotton or wool. The looped bristles can be made from monofilament yarns, multi-filament yarns, or spun yarns.

Further, the yarns can be shaped filaments, such as a multi-lobal shaped filament. As used herein "shaped" filaments or fibers refer to filaments or fibers not having a circular cross sectional shape. For example, a pentalobal filament can be used.

In accordance with the present invention, the looped bristles can be flavored or unflavored. Further, the looped bristles can be treated, such as with a fluoride compound or other additive described herein, or untreated.

Further, the looped bristles can be made from the same material as the base material on which the bristles are contained or can be made from a different material. For example, as described above, the bristles can be needle punched into a woven or non-woven backing layer. The loop material can also be made from a single layer of material or can be a laminate. For example, a base layer containing the looped bristles can be laminated to various other layers. For example, the base layer can be laminated to a woven layer, a knitted layer, a non-woven layer, an expandable layer such as spandex, a stretch bonded layer, or a neck bonded layer, or can be attached to various non-woven webs including spunbonded webs or spunbond-meltblown-spunbond laminate.

In order to alter the characteristics of the loop material, various post processing steps can also be performed in the material. For example, the material can undergo a shearing process, a napping process, a cleaning process, or a sanding process. During these processes some of the loops can be abraded and/or cut. For example, in one embodiment, a portion of the loops can be sheared. In another embodiment, these processing steps can be used not to cut the loops, but to fray the loops for making the bristles softer.

In one particular embodiment of the present invention, the loop material used in the finger glove is a loop material commonly used in hook and loop fasteners. For example, VELCRO loops No. 002 made by VELCRO, USA, Inc. can be used. This material is made with nylon loops. In an alternative embodiment, the looped fastener material can be elastic. Elastic woven loop materials include VEL-STRETCH Tape 9999 and MEDFLEX Tape 9399, both marketed by VELCRO, USA, Inc.

As described above, besides containing various non-elastic materials and, if desired, a texturized surface, the finger glove of the present invention can also contain an elastomeric component.

By containing such an elastomeric component, the finger glove of the present invention can better fit around a human finger. In this regard, referring to FIG. 2, one embodiment of the present invention is depicted that includes a finger glove made from a base web having at least one elastomeric component. In particular, the first section 20 is typically made from a base web that includes an elastomeric non-woven material. In some embodiments, both the second section 30 and the first section 20 are made from a base web having an elastomeric component. Further, in other embodiments, the finger glove 10 can be made from a unitary base web structure having an elastomeric component.

When present in the finger glove, the elastomeric component can take on various forms. For example, the elastomeric component can be elastic strands or sections uniformly or randomly distributed throughout the base web. Alternatively, the elastomeric component can be an elastic film or an elastic nonwoven web. The elastomeric component can also be a single layer or can be a multi-layer material.

In general, any material known in the art to possess elastomeric characteristics can be used in the present invention as an elastomeric component. Useful elastomeric materials can include, but are not limited to, films, foams, nonwoven materials, etc. For example, suitable elastomeric resins include block copolymers having the general formula A-B-A' or A-B, where A and A' are each a thermoplastic polymer endblock which contains a styrenic moiety such as a poly(vinyl arene) and where B is an elastomeric polymer midblock such as a conjugated diene or a lower alkene polymer. Block copolymers form the A and A' blocks, and the present block copolymers are intended to embrace linear, branched and radial block copolymers. In this regard, the radial block copolymers may be designated (A-B)m-X, wherein X is a polyfunctional atom or molecule and in which each (A-B)m- radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer," and particularly "A-B-A" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly (ethylene-butylene)/polystyrene) block copolymers. Commercial examples of such elastomeric copolymers are, for example, those known as KRATON® materials which are available from Shell Chemical Company of Houston, Tex. KRATON® block copolymers are available in several different formulations, a number of which are identified in U.S. Pat. Nos. 4,663,220, 4,323,534, 4,834,738, 5,093,422 and 5,304,599, hereby incorporated by reference.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly (ethylene-propylene) or SEPSEP elastomeric block copolymer available from the Shell Chemical Company of Houston, Tex. under the trade designation KRATON® G-1657.

Other exemplary elastomeric materials which may be used include polyurethane elastomeric materials such as, for example, those available under the trademark ESTANE® from B. F. Goodrich & Co. or MORTHANE® from Morton Thiokol Corp., polyester elastomeric materials such as, for example, those available under the trade designation HYTREL® from E. I. DuPont De Nemours & Company, and those known as ARNITEL®, formerly available from Akzo Plastics of Amhem, Holland and now available from DSM of Sittard, Holland.

Another suitable material is a polyester block amide copolymer having the formula:

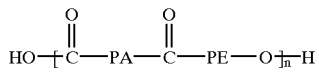

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 Mpa, as measured in accordance with ASTM D-790; a tensile strength at break of about 29 Mpa, a measured in accordance with ASTM D-639; and an elongation at break of about 650 percent as measured in accordance with ASTM D-638. Such materials are available in various grades under the trade designation PEBAX® from ELF Atochem Inc. of Glen Rock, N.J. Examples of the use of such polymers may be found in U.S. Pat. Nos. 4,724,184, 4,820,572 and 4,923,742 to Killian.

Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

The thermoplastic copolyester elastomers include copolyetheresters having the general formula:

percent to 750 percent when measured in accordance with ASTM D638 and a melt point of from about 350° F. to about 400° F. (176 to 205° C.) when measured in accordance with ASTM D-2117.

Commercial examples of such copolyester materials are, for example, those known as ARNITEL®, formerly available from Akzo Plastics of Amhem, Holland and now available from DSM of Sittard, Holland, or those known as HYTREL® which are available from E. I. DuPont de Nemours of Wilmington, Del. Formation of an elastomeric nonwoven web from polyester elastomeric materials is disclosed in, for example, U.S. Pat. No. 4,741,949 to Morman et al. and U.S. Pat. No. 4,707,398 to Boggs.

Elastomeric olefin polymers are available from Exxon Chemical Company of Baytown, Tex. under the trade name ACHIEVE® for polypropylene based polymers and EXACT® and EXCEED® for polyethylene based polymers. Dow Chemical Company of Midland, Mich. has polymers commercially available under the name ENGAGE®. Exxon generally refers to their metallocene catalyst technology as "single site" catalysts while Dow refers to theirs as "constrained geometry" catalysts under the name INSIGHT® to distinguish them from traditional Ziegler-Natta catalysts which have multiple reaction sites.

When incorporating an elastomeric component, such as described above, into a base web of the present invention, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

The elastic member used in neck bonded materials, stretch-bonded materials, stretch-bonded laminates, neck-bonded laminates and in other similar laminates can be made from materials, such as described above, that are formed into films, such as a microporous film, fibrous webs, such as a web made from meltblown fibers, or foams. A film, for example, can be formed by extruding a filled elastomeric polymer and subsequently stretching it to render it microporous.

Fibrous elastic webs can also be formed from an extruded polymer. For instance, as stated above, in one embodiment the fibrous web can contain meltblown fibers. The fibers can be continuous or discontinuous. Meltblown fabrics have been conventionally made by extruding a thermoplastic polymeric material through a die to form fibers. As the molten polymer fibers exit the die, a high pressure fluid, such as heated air or steam, attenuates the molten polymer filaments to form fine fibers. Surrounding cool air is induced into the hot air stream to cool and solidify the fibers. The fibers are then randomly deposited onto a foraminous surface to form a web. The web has integrity but may be additionally bonded if desired.

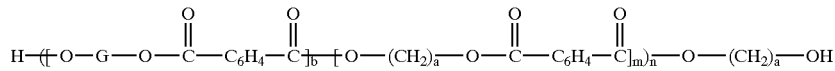

where "G" is selected from the group consisting of poly(oxyethylene)-alpha,omega-diol, poly(oxypropylene)-alpha,omega-diol, poly(oxytetramethylene)-alpha,omega-diol and "a" and "b" are positive integers including 2, 4 and 6, "m" and "n" are positive integers including 1–20. Such materials generally have an elongation at break of from about 600

Besides meltblown webs, however, it should be understood that other fibrous webs can be used in accordance with the present invention. For instance, in an alternative embodiment, elastic spunbond webs can also be formed from spunbond fibers. Spunbond webs are typically produced by heating a thermoplastic polymeric resin to at least its softening temperature, then extruding it through a spinnerette to form continuous fibers, which can be subsequently fed through a fiber draw unit. From the fiber draw unit the fibers are spread onto a foraminous surface where they are formed into a web and then bonded such as by chemical, thermal or ultrasonic means.

In one embodiment, the elastic member can be a neck stretched bonded laminate. As used herein, a neck stretched bonded laminate is defined as a laminate made from the combination of a neck bonded laminate and a stretch bonded laminate. Examples of necked stretched bonded laminates are disclosed in U.S. Pat. Nos. 5,114,781 and 5,116,662, which are both incorporated herein by reference. Of particular advantage, a neck stretch bonded laminate is stretchable in the machine direction and in a cross machine direction. Further, a neck stretch bonded laminate can be made with a nonwoven basing that is texturized. In particular, the neck stretched bonded laminate can be made so as to include a nonwoven facing that gathers and becomes bunched so as to form a textured surface. In this manner, the neck stretched bonded laminate can be used to form the entire finger glove having stretch characteristics in two directions and having a textured surface for cleaning the teeth and gums of a user.

Besides including a non-elastic component or an elastic component, the finger glove the present invention can further include a moisture barrier that is incorporated into or laminated to a base web of the present invention. Such a barrier can prevent, or at least minimize, leakage from outside the glove by establishing a barrier to the passage of liquid from the glove to the finger placed therein. For example, as shown in FIG. 4, a layer of material or film can be provided to form the moisture barrier 50, which can act as a barrier between the outer layer of the glove 10 and a finger. Moreover, in this embodiment, as shown in FIG. 4, a moisture barrier 50 can act as an inner lining for the second section 30 only, while the first section 20 possesses no such inner lining. However, it should also be understood that the moisture barrier 50 may be a liner for both the first section 20 and the second section 30. Moreover, the moisture barrier 50 can be applied asymetrically or unevenly to the glove such that one portion of the glove is substantially moisture-impervious, while another portion is not. It should be understood that a moisture barrier 50 can be applied to the glove 10 as a layer of the base web, or as an outer lining for the base web. Moreover, it should also be understood that the moisture barrier can be inherent within the base web structure such that it would not constitute a separate lining thereof.

In one embodiment of the present invention, the moisture barrier 50 can be made from liquid-impermeable plastic films, such as polyethylene and polypropylene films. Generally, such plastic films are impermeable to gases and water vapor, as well as liquids.

While completely liquid-impermeable films can prevent the migration of liquid from outside the glove to the finger, the use of such liquid- and vapor-impermeable barriers can sometimes result in a relatively uncomfortable level of humidity being maintained in a glove 10. As such, in some embodiments, breathable, liquid-impermeable barriers are desired. As used herein, the term "breathable" means that the barrier or film is pervious to water vapor and gases. In other words, "breathable barriers" and "breathable films" allow water vapor and gases to pass therethrough, but not necessarily liquids.

For instance some suitable breathable, liquid-impermeable barriers can include barriers such as disclosed in U.S. Pat. No. 4,828,556 to Braun et al., which is incorporated herein in its entirety by reference. The breathable barrier of Braun et al. is a multilayered, clothlike barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, meaning that it is substantially free of voids which connect the upper and lower surfaces of the film.

In other cases, various films can be constructed with micropores therein to provide breathability. The micropores form what is often referred to as tortuous pathways through the film. Liquid contacting one side of the film does not have a direct passage through the film. Instead, a network of microporous channels in the film prevents water from passing, but allows water vapor to pass.

In some instances, the breathable, liquid-impermeable barriers are made from polymer films that contain any suitable substance, such as calcium carbonate. The films are made breathable by stretching the filled films to create the microporous passageways as the polymer breaks away from the calcium carbonate during stretching. In some embodiments, the breathable film layers can be used in thicknesses of from about 0.01 mils to about 5 mils, and in other embodiments, from about 0.01 mils to about 1.0 mils.

An example of a breathable, yet fluid penetration-resistant material is described in U.S. Pat. No. 5,591,510 to Junker et al., which is incorporated herein by reference. The fabric material described in Junker et al. contains a breathable outer layer of paper stock and a layer of breathable, fluid-resistant nonwoven material. The fabric also includes a thermoplastic film having a plurality of perforations which allow the film to be breathable while resisting direct flow of liquid therethrough.

In addition to the films mentioned above, various other breathable films can be utilized in the present invention. One type of film that may be used is a nonporous, continuous film, which, because of its molecular structure, is capable of forming a vapor-permeable barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Although the inventors do not intend to be held to a particular mechanism of operation, it is believed that films made from such polymers solubilize water molecules and allow transportation of those molecules from one surface of the film to the other. Accordingly, such films may be sufficiently continuous, i.e., nonporous, to make them liquid-impermeable but still allow for vapor permeability.

Still, other breathable, liquid-impermeable barriers that can be used in the present invention are disclosed in U.S. patent application Ser. No. 08/928,787 entitled "Breathable, Liquid-impermeable, Apertured Film/Nonwoven Laminate and Process for Making the Same", which is incorporated herein in its entirety by reference. For example, breathable films and/or apertured films can be utilized in the present invention. Such films can be made within a laminate structure. In one embodiment, a breathable, liquid-impermeable, apertured film/nonwoven laminate material can be formed from a nonwoven layer, an apertured film layer, and a breathable film layer. The layers may be arranged so that the apertured film layer or the breathable film layer is attached to the nonwoven layer.

For instance, in one embodiment, an apertured film can be used in the present invention that is made from any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

Moisture barrier layers, as described above, can be used alone or incorporated into a laminate when used to construct the finger glove of the present invention. When incorporate into a laminate, the laminate can include various nonwoven webs in combination with the moisture barrier layer. For instance, moisture barrier laminates can be formed from many processes, such as for example, meltblowing processes, spunbonding processes, coforming processes, spunbonding/meltblowing/spunbonding processes (SMS), spunbonding/meltblowing processes (SM), and bonded carded web processes. For instance, in one embodiment, the nonwoven layer of a laminate moisture barrier of the present invention is a spunbond/meltblown/spunbond (SMS) and/or spunbond/meltblown (SM) material. An SMS material is described in U.S. Pat. No. 4,041,203 to Brock et al. which is incorporated herein in its entirety by reference. Other SMS products and processes are described for example in U.S. Pat. Nos. 5,464,688 to Timmons et al., 5,169,706 to Collier et al. and 4,766,029 to Brock et al., all of which are also incorporated herein in their entireties by reference. Generally, an SMS material will contain a meltblown web sandwiched between two exterior spunbond webs. Such SMS laminates are available from Kimberly-Clark Corporation under marks such as Spunguard® and Evolution®. The spunbonded layers on the SMS laminates provide durability and the internal meltblown barrier layer provides porosity and additional clothlike feel. Similar to an SMS laminate, an SM laminate is a spunbond layer laminated to a meltblown layer.

In forming a finger glove of the present invention with a moisture barrier, the barrier can be bonded together with the other layers of the wipe in a number of various ways. Thermal bonding, adhesive bonding, ultrasonic bonding, extrusion coating, and the like, are merely examples of various bonding techniques that may be utilized in the present process to attach the moisture barrier to the fibrous layers of the finger glove.

In some embodiments, any of the above layers and/or materials can also be dyed or colored so as to form a base web or moisture barrier having a particular color. For example, in one embodiment, the moisture barrier 50 can be provided with a colored background. For instance, white tufts, colored tufts, and/or a white titanium oxide background could be utilized.

As described above, the finger glove of the present invention can be made from various components that contain various features. For instance, the finger glove can include a non-elastic component, an elastic component, a moisture barrier. If desired, a texturized surface can be located on the finger glove for facilitating the scrubbing and brushing of teeth and gums. Further, the finger glove can be made from single layer materials or laminates which, in turn, can be made from various materials and fibers. One particular embodiment of a finger glove made in accordance with the present invention will now be discussed with reference to FIG. 2.

In this embodiment, the finger glove 10 includes the first section 20 thermally bonded to the second section 30. The second section 30 is designed for contacting the teeth and gums of the user, while the first section 20 is made from an elastic laminate for providing the finger glove with form-fitting properties.

More particularly, the second section, in this embodiment, is a three layer laminate. The laminate includes an interior polypropylene spunbond layer, a middle moisture barrier layer, and an outer bi-component spunbond layer that forms an exterior surface of the finger glove.

The polypropylene spunbond layer is made from spunbond polypropylene filaments and can have a basis weight of from about 0.3 osy to about 1.0 osy, and can particularly have a basis weight of about 0.5 osy. The moisture layer, on the other hand, can be a film made from linear low-density polyethylene containing a calcium carbonate filler. The film can be stretched in order to create pores for making the film breathable while remaining substantially impermeable to liquids. The moisture barrier layer can have a basis weight of from about 0.2 osy to about 1.0 osy, and particularly can have a basis weight of from about 0.5 osy. The polypropylene spunbond layer can be adhesively secured through the moisture barrier layer.

In an alternative embodiment, the interior polypropylene spunbond layer can be replaced with a nonwoven web made from polypropylene/polyethylene bicomponent fibers. The middle moisture barrier layer, on the other hand, can be a film made from a mixture of polymers, such as CATALLOY film marketed by the Pliant Corporation.

The exterior layer can be a spunbond or through air bonded web made from bi-component polyethylene/polypropylene filaments in a side-by-side arrangement. The exterior layer can have a basis weight from about 1.0 osy to about 5.0 osy, and can particularly have a basis weight of from about 2.0 osy to about 4.0 osy. Alternatively, the exterior layer itself can be a layered or laminate structure. For example, a two-banked process can be used in which a layer of larger diameter fibers is formed on a layer of small diameter fibers.

The exterior bi-component spunbond layer can be laminated to the other layers using a thermal point bonding process, such as a point unbonded pattern process. More particularly, the layers can be point unbonded to form a texturized surface. For instance, as shown in FIG. 2, the point unbonded pattern can be designed to form circular tufts which protrude from the surface of the laminate.

As mentioned above, the first section 20 is an elastic laminate. For instance, the first section 20 can be a stretch bonded laminate sheet. The stretch bonded laminate sheet can include elastic threads made from an elastomeric material sandwiched between two polypropylene spunbond layers. The elastic threads can be, for instance, made from a styrene-ethylene butylene-styrene block copolymer, such as KRATON G 2740, available from the Shell Chemical Company. The stretch-bonded laminate can have a basis weight of from about 1.0 osy to about 5 osy, particularly from about 1.5 osy to about 3.5 osy, and more particularly from about 2.0 osy to about 3.0 osy.

Instead of a stretch bonded laminate sheet, the first section 20 can also be a neck bonded laminate sheet. The neck bonded laminate sheet can include a metallocene catalyzed elastic polyethylene film sandwiched between two polypropylene spunbond layers. The spunbond layers can have a basis weight of about 0.45 osy prior to being stretched. The polyethylene film, on the other hand, can have a basis weight from about 0.5 osy to about 1.5 osy.

The first section 20 can be attached to the second section 30 using various methods. For example, as shown in FIG. 2, the first section 20 can be ultrasonically bonded to the second section 30 along the other edges in order to form a pocket for the insertion of a finger.

Once the first section 20 and the second section 30 are bonded together, excess material can be cut and removed from the finger glove. In general, any suitable cutting method can be used in order to trim away excess material. For example, the material can be cut using a high pressure jet of water referred to as a water knife or can be cut using a conventional mechanical device, such as a cutter or a pair of shears. In one embodiment, the first section 20 and the second section 30 can be simultaneously bonded together and cut from the materials from which they are made. For instance, ultrasonic energy can be used to bond and cut materials in one step.

The dimensions of the finger glove that is formed in accordance with the present invention will depend upon the particular application and purpose for which the finger glove is to be used. For instance, the finger glove can be constructed in order to fit around the finger of an adult or the finger of a child. Further, the finger glove can also be constructed to fit around two fingers. For most single finger gloves, the wipe should have a length of from about 1 inch to about 5 inches and a median flattened width of from about 0.5 inches to about 1.5 inches. When constructed to fit around two fingers, the finger glove can have a median width of from about 0.75 inches to about 2.5 inches, depending on the elasticity of the wipe.

Figure 13:
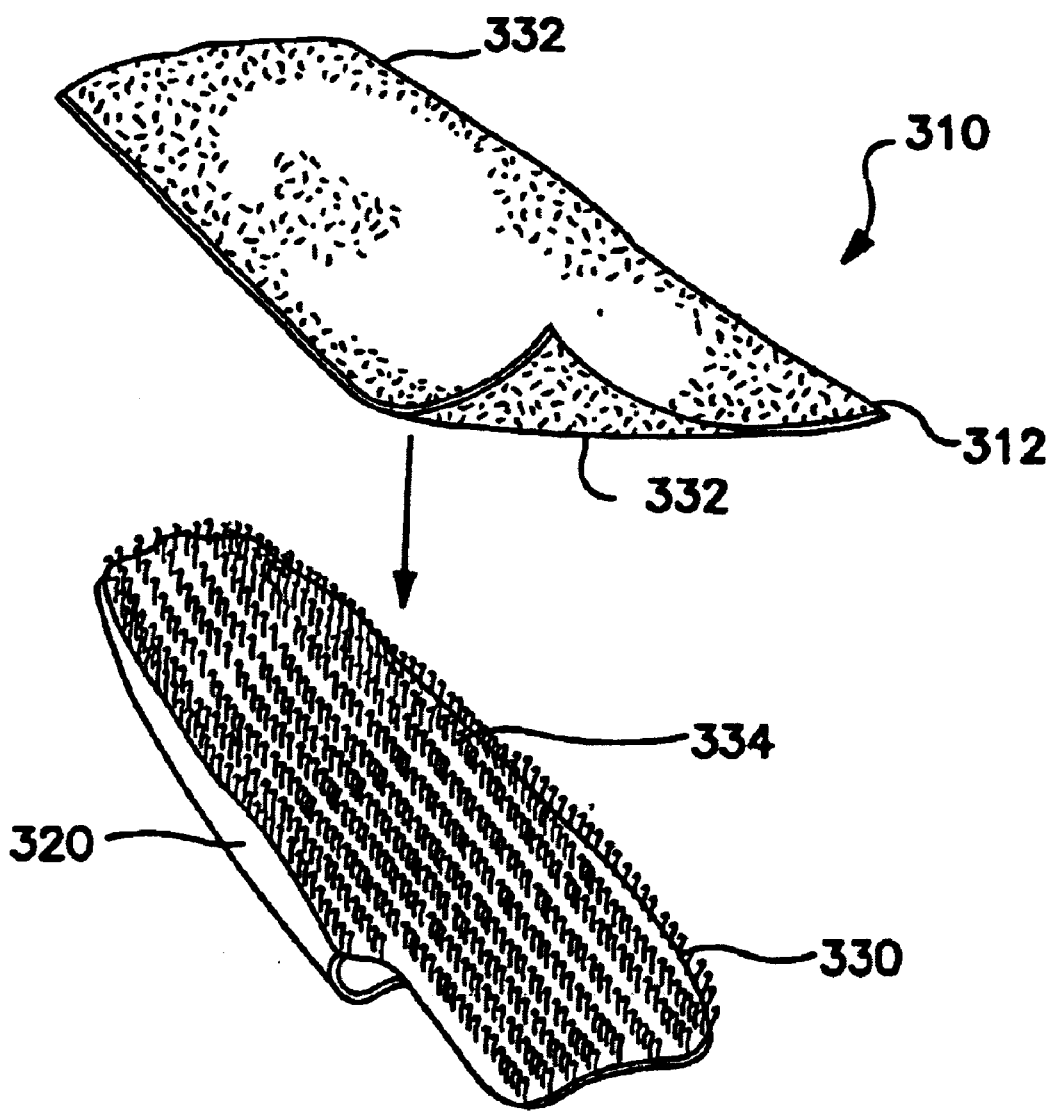
FIG. 13 is a perspective view of another alternative embodiment of a finger glove made in accordance with the present invention.

Referring now to FIGS. 11–13, three further embodiments of finger gloves made in accordance with the present invention are shown. In these embodiments, the texturized material is a looped material. For instance, referring to FIG. 11, a finger glove generally 110 is shown. The finger glove 110 includes a first section 120 thermally bonded, stitched or otherwise connected to a second section 130. The second section 130 includes a texturized surface which is a looped material containing a plurality of bristles 132.

In this embodiment, the looped material 130 represents a knitted fabric. The looped bristles 132 are arranged in a systematic pattern on the material. In particular, the looped bristles 132 form rows along the surface of the finger glove 110.

As shown in FIG. 11, the bristles 132 are located over the entire surface of the second section 130. It should be understood, however, that the looped bristles can be placed in a particular area, such as only at the tip of the finger glove or over all surfaces of the finger glove. For example, the area occupied by the looped bristles can have a circular, oval or any other suitable shape.

The first section 120 can be made from various materials. For example, in one embodiment, the first section 120 can be made from an elastic material, such as a stretch bonded laminate.

Referring to FIG. 12, another alternative embodiment of a finger glove generally 210 is shown. In this embodiment, the finger glove 210 is configured to fit around a pair of fingers 212.

The finger glove 210 includes a first section 220 and a second section 230. The second section 230 is a looped material containing looped bristles 232. In this embodiment, the looped bristles 232 are densely packed on the looped material 230 and are randomly arranged. The looped material 230 is similar to a loop material used in a hook and loop fastener. As shown, the loop material 230 not only includes looped bristles 232 but also a base layer 234. The base layer 234 can be made from various fabrics, including elastic fabrics, such as spandex fabrics.

Referring to FIG. 13, a further alternative embodiment of a finger glove generally 310 is shown. In this embodiment, the finger glove 310 includes a first section 320 connected to a second section 330. The second section 330 includes a plurality of hooks 334. In one embodiment, the surface containing the hooks could be used for cleaning an adjacent surface.

In an alternative embodiment, the finger glove 310 further includes a looped material 312 containing looped bristles 332. As shown, the looped bristles 332 are disposed about both sides of the looped material 312. In this manner, one side of the looped material 312 can be attached to the second section 330 through a hook and loop fastening mechanism. Once applied to the second section 330, the looped material can then be used as a cleaning surface.

In this embodiment, the loop material 312 can be removed from the finger glove 310 and replaced as desired. Consequently, this embodiment generally refers to a finger glove having a reusable component.

In an alternative embodiment to the finger glove illustrated in FIG. 13, the second section 330, instead of including a plurality of hooks 334, can be made from a nonwoven material defining a loop fastening-like surface. In this embodiment, the material 312 can include looped bristles 332 on one side of the material and can include hook fasteners on the opposite side of the material. In this manner, the hooks located on the material 312 can be secured to the surface of the second section 330.

In the embodiments illustrated in FIGS. 11, 12 and 13, the material containing the loop bristles can either be non-elastic or elastic. When using an elastic material containing loop bristles, however, the entire finger glove can be made from the material. For example, the elastic material containing the loop bristles, such as VELSTRETCH Tape, 9999 or MEDFLEX Tape, 9399 available from VELCRO, USA, Inc., can be formed into a tubular shape and then bonded along the edges. The resulting product will have form-fitting properties and will have an exterior, scrubbing surface comprised of the looped bristles.

In still a further embodiment, hook structures can be laminated to the backing of an elastic material containing loop bristles as described above. In this embodiment, the elastic looped material can be wrapped around a finger and secured to itself using the hook structures. Once secured to a finger, the material can be used to scrub an adjacent surface.

In general, a finger glove can also be applied with a variety of chemical additives. For instance, any material, chemical, or additive commonly applied by cotton ball, swabs, or gauzes can be applied to a finger glove of the present invention. Examples of such additives can include, but are not limited to, medications, diaper rash ointments, alcohols, oral anesthetics, facial make-up removal agents, and the like.

In addition, various other additives, chemicals, and materials can be applied to a finger glove of the present invention. For instance, certain additives can be when the finger glove is used as an oral cleaning device. For example, in one embodiment, cationic polymers can be coated onto the finger glove. Cationic polymers can help clean teeth and/or gums because they typically have a strong attraction for negatively charged bacteria and deleterious acidic byproducts that accumulate in plaque. One example of a cationic polymer that is suitable for use in the present invention is chitosan (poly-N-acetylglucosamine, a derivative of chitin) or chitosan salts. Chitosan and its salts are natural biopolymers that can have both hemostatic and bacteriostatic properties. As a result, chitosan can help reduce bleeding, reduce plaque, and reduce gingivitis.

In addition to chitosan and chitosan salts, any other cationic polymer known in the art can generally be applied to a finger glove of the present invention. For example, in one embodiment, cationic starches are used in the present invention. One such suitable cationic starch is, for example, COBOND, which can be obtained from National Starch. In another embodiment, cationic materials that are oligomeric compounds can be used. In some embodiments, combinations of cationic materials can be utilized.

In addition to the chemical additives mentioned above, a variety of other additives can be applied to a finger glove of the present invention. For instance, other well known dental agents can be utilized. Examples of such dental agents include, but are not limited to alginates, soluble calcium salts, phosphates, flourides, such as sodium flouride (NaF) or stannous flouride ($SnF_2$), and the like. Moreover, mint oils and mint oil mixtures can be applied to a finger glove of the present invention. For instance, in one embodiment, peppermint oil can be applied to the finger glove. Moreover, in another embodiment, a mint oil/ethanol mixture can be applied. Components of mint oil (e.g., menthol, carvone) can also be used. Additionally, various whitening agents can be applied to the finger glove. Examples of whitening agents include peroxides and in situ sources of peroxide, such as carbamide peroxide.

Furthermore, in some embodiments, the finger glove can also comprise an anti-ulcer component. In particular, one embodiment of the present invention can comprise a component designed to act as an anti-*H. pylori* agent. In general, any additive known in the art to be an anti-ulcer or anti-*H. pylori* agent can be used in the present invention. In one embodiment, for example, bismuth salts can be utilized. One particularly effective bismuth salt, bismuth subcitrate, is described in more detail in U.S. Pat. No. 5,834,002 to Athanikar, which is incorporated herein in its entirety by reference thereto. Another example of a suitable bismuth salt is PEPTO-BISMOL sold by The Procter & Gamble Company, containing bismuth subsalicylate. In addition to bismuth salts, other examples of suitable anti-ulcer additives include, but are not limited to, tetracycline, erythromycin, clorithromycin or other antibiotics. Furthermore, any additive useful for treating peptic ulcers, such as H2-blockers, omeprazole, sucralfate, and metronidazole, can be used as well.

Besides the additives mentioned above, other additives can also be applied to the glove. Such materials can include, but are not limited to, flavoring agents, anti-microbial agents, preservatives, polishing agents, hemostatic agents, surfactants, etc. Examples of suitable flavoring agents include various sugars, breath freshening agents, and artificial sweeteners as well as natural flavorants, such as cinnamon, vanilla and citrus. Moreover, in one embodiment, xylitol, which provides a cooling effect upon dissolution in the mouth and is anti-cariogenic, can be used as the flavoring agent. As stated, preservatives, such as methyl benzoate or methyl paraben, can also be applied to a finger glove of the present invention. The additives can be applied to the finger glove as is or they can be encapsulated in order to preserve the additives and/or to provide the additive with time release properties.

In addition, a variety of other additives and combinations thereof can be applied to a finger glove of the present invention. For instance, examples of various materials that can be utilized as additives in the present invention are described in U.S. Pat. Nos. 3,902,509 to Tundermann et al. and 5,445,825 to Copelan et al., which are incorporated herein by reference. Although various specific additives have been specifically mentioned above, it should be understood that any additive can generally be applied to a finger glove of the present invention. The additives can be applied to the finger glove as is or they can be encapsulated in order to preserve the additives and/or to provide the additive with time release properties.

In general, the chemical additives described above can be applied to a finger glove of the present invention according to a number of ways known in the art. For example, the additives can be applied to the glove using a saturant system, such as disclosed in U.S. Pat. No. 5,486,381 to Cleveland et al., which is incorporated herein by reference. Moreover, the additives can also be applied by print, roll, blade, spray, spray-drying, foam, brush treating applications, etc., which are all well known in the art.

The additives can further be applied as a mixture of molten solids or co-extruded onto the glove. Additionally, in another embodiment, the chemical additives can be impregnated into the material during manufacturing as is well known in the art. It should be understood that when coated onto a glove as described above, the additives can be applied to the base web before or after the base web is stamped or bonded to form a finger glove of the present invention. Furthermore, it should also be understood that, if desired, various additives, solutions, and chemicals can be applied by the consumer to the glove just before use.

In another embodiment, the additive is encapsulated and then applied to the finger glove. Encapsulation is a process by which a material or mixture of materials is coated with or entrapped within another material or mixture of materials. The technique is commonly used in the food and pharmaceutical industries. The material that is coated or entrapped is normally a liquid, although it can also be a solid or gas, and is referred to herein as the core material. The material that forms the coating is referred to as the carrier material. A variety of encapsulation techniques are well-known in the art and can be used in the current invention, including spray drying, spray chilling and cooling, coacervation, fluidized bed coating, liposome entrapment, rotational suspension separation, and extrusion.

Spray drying is commonly used for encapsulating food and flavors. To prepare a material for spray drying, the carrier material is dissolved in an aqueous solution. The core ingredient is added to this solution and mixed thoroughly. A typical load of carrier to core material is 4:1, although much higher or lower loads can be used. The mixture is homogenized, and then fed into a spray dryer where it is atomized and released into a stream of hot air. The water is evaporated, leaving a dried particle comprising the core material trapped within the carrier matrix.

Suitable carrier materials include but are not limited to gums, gum Arabic, modified starches, gelatin, cellulose derivatives, and maltodextrins. Suitable core materials include but are not limited to flavors, natural oils, additives, sweeteners, stabilizers besides the other various additives mentioned above.

Regardless of the mechanism utilized to apply the chemical additives to the glove, the additives can be applied to the glove via an aqueous solution, non-aqueous solution, oil, lotion, cream, suspension, gel, etc. When utilized, an aqueous solution can contain any of a variety of liquids, such as various solvents and/or water. Moreover, the solution can often contain more than one additive. In some embodiments, the additives applied by an aqueous solution or otherwise constitute approximately less than 80% by weight of the finger glove. In other embodiments, the additives can be applied in an amount less than about 50% of the weight of the glove.

Moreover, in some embodiments, the additives can also be applied asymmetrically onto the glove to reduce costs and maximize performance of the glove. For instance, in one embodiment, a flat sheet of the base web is asymmetrically contacted with a particular coating agent, and thereafter stamped and bonded to form a finger glove of the present invention, wherein only the surface used to clean teeth is coated with the additives. In another embodiment, the finger glove is stamped and bonded, and thereafter asymmetrically coated with a particular coating agent.

Prior to being shipped and sold, the finger glove of the present invention can be placed in various sealed packaging in order to preserve any additives applied to the finger glove or otherwise to maintain the finger glove in a sterile environment. Various packaging materials that can be used include ethylene vinyl alcohol (EVA) films, film foil laminates, metalized films, multi-layered plastic films, and the like. The packaging can be completely impermeable or can be differentially permeable to the flavorants depending on the application.

The present invention may be better understood by reference to the following examples:

EXAMPLES

Various finger gloves were made according to the present invention and tested. The finger gloves were made with various materials as described in the following examples. The finger gloves were constructed from the materials using ultrasonic welding to form the seams. In each of the following examples, unless otherwise specified, each finger glove was made from a mold having a length of from about 2.75 inches to about 3.0 inches. The finger gloves were made with an open end for the insertion of a finger and a closed end. The flattened width of the finger glove tapered inwardly from the open end to the closed end. The width of the mold at the opening ranged from 1.063 inches to 1.25 inches. The width at the closed end ranged from 0.8 inches to 0.9 inches. After being formed, the finger gloves were cut to a length of from 1.0 inches to 3.0 inches. The width at the opening normally ranged from 0.6 inches to 1.0 inches (internal diameter). When containing a pull-on tab, the length of the tab ranged from 0.2 to 0.8 inches.

Example 1

A finger glove of the present invention was formed as follows. Specifically, a first section made from a point unbonded spunbond laminate material was ultrasonically welded to a stretch-bonded laminate (SBL) sheet using a Branson 920 IW ultrasonic welder. The point unbonded spunbond laminate formed the front of the finger glove, while the SBL sheet formed the back of the finger glove.

The point unbonded spunbond laminate was formed by thermally bonding together a polypropylene spunbond web, a breathable film sheet, and a bicomponent spunbond web. The breathable film sheet was placed in between the spunbond webs.

The polypropylene spunbond web had a basis weight of 0.5 osy. The bicomponent spunbond web was made from bicomponent filaments having a polyethylene component and a polypropylene component in a side-by-side relationship. The bicomponent spunbond web had a basis weight of 2.5 osy. The breathable film sheet was made from a linear low density polyethylene containing a calcium carbonate filler. The film was stretched in order to create a microporous film. The film had a basis weight of 0.5 osy.

The bicomponent spunbond web was thermally bonded to the film laminate using a point-unbonded pattern that created texture. In particular, circular tufts were formed on the bicomponent spunbond web side of the laminate. During bonding, a top bond roll having the point-unbonded pattern was heated to 260° F. while a bottom bond roll was heated to 240° F.

The SBL sheet, on the other hand, included threads of an elastic material sandwiched between two polypropylene spunbond layers. The elastic material used was KRATON G2740 S-EB-S block copolymer available from the Shell Oil Company. The SBL sheet had a basis weight of 2.5 osy. An imprinted, magnesium bond plate served as an anvil for ultrasonic bonding of the SBL sheet to the point unbonded spunbond laminate.

The bicomponent spunbond layer of the point unbonded spunbond material was placed adjacent to the SBL sheet during the ultrasonic welding process, which placed the textured nubs against the SBL sheet. After ultrasonic welding, excess material was trimmed around the edges and the finger glove was inverted to place the seam on the inside and the textured nubs on the outside. Peppermint oil was applied to the finger glove, which was subsequently used to clean the mouth of an adult.

Example 2

A finger glove as described in Example 1 was constructed and treated with peppermint oil. The finger glove was then subsequently used by an adult to clean the mouth of a toddler.

Example 3

A finger glove made according to Example 1 was constructed. The finger glove was dipped into drippings from sliced steak and then used by an adult to clean the mouth of a dog.

Example 4

A finger glove as described in Example 1 was constructed. In this example, however, the bicomponent spunbond sheet of the point unbonded spunbond laminate had a basis weight of 3.6 osy. During the point unbonded process, the top bond roll was heated to 270° F., while the bottom bond roll was heated to 240° F. After being formed, the finger glove was inverted and treated with peppermint oil. The finger glove was then subsequently used to clean the mouth of an adult.

Example 5

A finger glove was constructed similar to the finger glove described in Example 1. In this embodiment, however, the bicomponent spunbond sheet of the point unbonded spunbond laminate was a through air bonded bicomponent fibrous web having a basis weight of 1.8 osy. The bicomponent filaments contained a polyethylene component and a polypropylene component in a side-by-side relationship. During the point unbonded process, the top bond roll was heated to 260° F. while the bottom bond role was heated to 240° F. After the finger glove was formed, the glove was inverted so that the textured nubs as described in Example 1 were placed on the outside.

Example 6

A finger glove as described in Example 5 was constructed. In this example, however, the through air bonded bicomponent fibrous web had a basis weight of 2.5 osy. Further, the bicomponent web was yellow-pigmented.

Example 7

A finger glove as described in Example 1 was constructed. In this example, however, the point unbonded spunbond laminate was replaced with a multi-layered material that included a spunbond-meltblown-spunbond laminate that was adhesively laminated to a strip of loop material from a hook and loop fastener. The spunbond-meltblown-spunbond laminate had a total basis weight of 1.0 osy. The laminate included a 0.4 osy meltblown interior layer made from polypropylene fibers. The two spunbond facings were also made from polypropylene.

The loop material was VELCRO loop 2000 material obtained from VELCRO USA, Inc.

The resulting multi-layered material was ultrasonically welded to the stretch-bonded laminate described in Example 1, such that the spunbond-meltblown-spunbond layer was positioned adjacent to the stretch-bonded layer. The loop material formed a facing of the finger glove. The finger glove was then treated with a flavor formulation containing spearmint and peppermint and was subsequently used to clean the mouth of an adult.

Example 8

A finger glove as described in Example 1 was constructed and used to remove make-up. In this example, however, the point unbonded spunbond laminate was replaced with a coform sheet. The coform sheet was a meltblown web containing 50% pulp fibers and 50% by weight polypropylene fibers. The coform sheet had a basis weight of 1.2 osy. The coform sheet was ultrasonically welded to the stretch-bonded laminate described in Example 1.

In this example, the finger glove was not inverted. Further, the section of the finger glove made from the coform sheet was longer than the section made from the stretch-bonded laminate creating a pull-on tab. The finger glove was then subsequently dipped in alcohol and used to remove make-up.

Example 9

A finger glove was constructed similar to the finger glove described in Example 1. In this example, the bicomponent spunbond web contained in the point unbonded spunbond laminate had a basis weight of 3.5 osy. During the point unbonded process, the top bond roll was heated to 270° F., while the bottom bond roll was heated to 250° F.

In contrast to Example 1, however, instead of using a stretch-bonded laminate sheet, the point unbonded spunbond laminate was ultrasonically welded to a neck-bonded laminate. The neck-bonded laminate was formed by adhesively bonding a 15 gsm polyurethane film between a pair of opposing polypropylene spunbond facings. The adhesive used to form the neck-bonded laminate was Findley H2525A adhesive obtained from Findley, Inc. The spunbond facings had a basis weight of 0.5 osy prior to being stretched or necked. The spunbond facings were necked to a width corresponding to 30% of their original width.

After the point unbonded spunbond laminate was welded to the neck-bonded laminate, the finger glove was inverted so that the textured nubs formed an exterior face of the finger glove. Peppermint oil was then applied to the finger glove which was subsequently used to clean the mouth of an adult.

Example 10

A finger glove was constructed similar to the finger glove described in Example 1, using the same point unbonded spunbond laminate. In contrast to Example 1, however, instead of using a stretch-bonded laminate as the elastic material, a neck-bonded laminate was used. The point unbonded spunbond laminate was ultrasonically welded to the neck-bonded laminate.

The neck-bonded laminate contained a 35 gsm metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 45% of the original width.

After the point unbonded spunbond laminate was welded to the neck-bonded laminate, the finger glove was inverted so that the textured nubs formed an exterior face of the finger glove. Peppermint oil was then applied to the finger glove which was subsequently used to clean the mouth of an adult.

Example 11

A finger glove similar to the finger glove described in Example 9 was constructed. In this example, however, the neck-bonded laminate sheet was formed by adhesively bonding a 15 gsm polyether amide elastic film (PEBAX-2533 film obtained from Elf Atochem) to a pair of opposing bidirectionally extensible polypropylene spunbond facings. The polypropylene spunbond facings had a basis weight of 0.3 osy prior to being stretched or necked. When attached to the elastic film, the spunbond facings were necked to a width corresponding to 40% of their original width and then crimped an amount to produce a 50% reduction in length.

The neck-bonded laminate was ultrasonically welded to the point unbonded spunbond laminate. The resulting finger glove was inverted and treated with peppermint oil. It was observed that the neck-bonded laminate sheet had elastic properties in two dimensions. The finger glove was subsequently used to clean the mouth of an adult.

Example 12

A finger glove as described in example 1 was constructed from a point unbonded spunbond laminate ultrasonically welded to a stretch-bonded laminate. The total basis weight for the point unbonded spunbond sheet was 2.75 osy.

The finger glove was applied with the following additive.

| Additive | Wt % |
|---|---|
| Peppermint oil (obtained from Global Essence, Inc.) | 0.51 |
| 1% Chitosan citrate solution (formed from chitosan made by Vanson Chemical Company and citric acid made by Archer Daniels Midland) | 0.07 |
| T MAZ-80 Polysorbate Surfactant (obtained from BASF) | 0.55 |
| Xylitol (obtained from Cultor, Inc.) | 8.56 |
| Water | 90.31 |

After being immersed in the above aqueous solution, the finger wipe was allowed to dry and sealed in a plastic film. After a period of time, the finger wipe was removed and used in the mouth of a subject.

Example 13

A finger glove similar to the one described in example 1 was constructed. In this example, the point unbonded laminate had a total basis weight of 2.75 osy. Further, instead of being welded to a stretch-bonded laminate, the point unbonded laminate was adhesively secured to a elastomeric, melt blown polyether ester (ARNITEL EM400 polyether ester obtained from DSM Engineering Plastics). The melt blown polyether ester web had a basis weight of about 2 osy.

Example 14

A finger glove similar to the one described in example 1 was constructed. In this embodiment, the point unbonded laminate had a total basis weight of 2.75 osy.

In this example, the point unbonded laminate was welded to a spunbond-meltblown-spunbond laminate that had been adhesively bonded to a thin strip of an elastic material commonly used as leg elastics in diapers. Specifically, the spunbond-meltblown-spunbond laminate had a total basis weight of 1.0 osy wherein the meltblown interior layer had a basis weight of 0.4 osy. The elastic strip was 1 centimeter in width and was adhesively bonded to the spunbond-meltblown-spunbond laminate. The elastic strip included elastic threads sandwiched between two polypropylene spunbond facings.

The resulting finger glove made by welding the spunbond-meltblown-spunbond laminate to the point unbonded spunbond sheet was elastic because of the elastic strip attached spunbond-meltblown-spunbond laminate. The elastic strip was not uniformly elastic. The finger glove was made so that the elastic strip rested between the first and second knuckles of the finger of an adult after insertion of the finger into the finger glove.

Example 15

An alternative embodiment of a finger glove made in accordance with the present invention was formed as follows. In this example, the finger glove included a first section made from a spunbond-meltblown-spunbond laminate welded to a second section made from a neck-bonded laminate. The spunbond-meltblown-spunbond laminate formed the front side of the finger glove, while the neck-bonded laminate formed the back side.

The spunbond-meltblown-spunbond laminate was made from polypropylene and had a total basis weight of 0.8 osy.

The neck-bonded laminate on the other hand, was similar to the neck-bonded laminate described in Example 10, except that it had a heavier weight film and heavier weight facings. Further, the facings were necked to a width 40% of their original width. The laminate had an overall basis weight of 4.2 osy.

The two sections were thermally bonded together in the shape of a finger and excess material was trimmed from the edges of the wipe. The wipe was thereafter inverted to place the seams on the inside. The spunbond-meltblown-spunbond laminate section of the finger glove was longer than the neck-bonded laminate section, such that a pull-on-tab was provided for ease in placing the wipe on a finger. Specifically, the length of the spunbond-meltblown-spunbond laminate section was approximately 5 centimeters while the length of the neck-bonded laminate was approximately 4 centimeters. Upon flattening of the finger glove, the width at the bottom of the wipe was approximately 2.4 centimeters.

Example 16

An alternative embodiment of a finger glove made in accordance with the present invention was formed as follows. In this example, the finger glove included a first section made from a spunbond-meltblown-spunbond laminate welded to a second section made from a neck-bonded laminate. The spunbond-meltblown-spunbond laminate formed the front side of the finger glove, while the neck-bonded laminate formed the back side.

The spunbond-meltblown-spunbond laminate was made from polypropylene and had a total basis weight of 0.8 osy.

The neck-bonded laminate on the other hand, was similar to the neck-bonded laminate described in Example 10, except that it had a heavier weight film and heavier weight facings to have an overall basis weight of 4.2 osy. Further, the facings were necked to a width 40% of their original width.

The two sections were thermally bonded together in the shape of a finger and excess material was trimmed from the edges of the wipe. The wipe was thereafter inverted to place the seams on the inside. The spunbond-meltblown-spunbond laminate section of the finger glove was longer than the neck-bonded laminate section, such that a pull-on-tab was provided for ease in placing the wipe on a finger. Specifically, the length of the spunbond-meltblown-spunbond laminate section was approximately 5 centimeters while the length of the neck-bonded laminate was approximately 4 centimeters. Upon flattening of the finger glove, the width at the bottom of the wipe was approximately 2.4 centimeters.

Example 17

A finger glove was constructed similar to the finger glove in Example 1, insofar as an elastic material was welded to a texturized surface with a finger-shaped design. In contrast to Example 1, however, instead of using a stretch bonded laminate as the elastic material, a neck-bonded laminate was used. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

In further contrast to Example 1, the texturized material was not a point unbonded nonwoven, but rather a knitted nylon material having looped bristles approximately 3 to 4 mm in length. This knitted material had a basis weight of approximately 2.5 osy. The bristles had a consistent directional component, allowing scrubbing in a direction with relatively high or low coefficient of friction, i.e., both with and against "the grain". The looped bristles were fairly homogeneous in size and distribution, and generally extended between 3 mm and 4 mm from the surface. The bristle loops were comprised of multiple filaments.

The knitted material was ultrasonically welded to the neck-bonded laminate. Peppermint oil was then applied to the finger glove, which was subsequently used to clean the mouth of an adult.

Example 18

A finger glove was constructed similar to the finger glove in Example 1, insofar as an elastic material was welded to a texturized surface with a finger-shaped design. In contrast to Example 1, however, instead of using a stretched bonded laminate as the elastic material, a necked bonded laminate was used. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

In further contrast to Example 1, the texturized material was not a point unbonded nonwoven, but rather a knitted nylon material having looped bristles approximately 3 mm in length. This knitted material had a basis weight of approximately 2.5 osy, and was ultrasonically welded around the perimeter to a breathable film laminate (1.0 osy), thereby providing a nonwoven/knit laminate containing looped bristles and a moisture barrier.

The bristled, nonwoven/knit laminate was ultrasonically welded to the neck-bonded laminate such that the looped bristles were adjacent to the NBL. The finger glove was inverted, placing the seam on the inside and the bristles on the outside. A commercially available baby toothpaste (GERBER Tooth & Gum Cleanser) was then applied to the finger glove, which was subsequently used to clean the mouth of a toddler.

Example 19

A finger glove was constructed similar to the finger glove in Example 1. The point unbonded spunbond laminate was ultrasonically welded to a neck-bonded laminate. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

In further contrast to Example 1, the texturized material was a conventional loop fastener, VELCRO Med-Flex Tape 9399, comprised of nylon and Spandex. This material was elastic. The looped bristles were monofilament, and generally extended from 0.5 mm to 3 mm from the surface when unstretched, with some extending to 10 mm when tension was applied.

The knitted material was ultrasonically welded to the neck-bonded laminate. Peppermint oil was then applied to the finger glove which was subsequently used to clean the mouth of an adult.

Example 20

A finger glove was constructed similar to the finger glove in Example 1. In contrast to Example 1, however, instead of using a stretch bonded laminate as the elastic material, a neck-bonded laminate was used. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

In further contrast to Example 1, the texturized material was a laminate comprised of a commercially available loop fastener, VELCRO Loop 002 Tape 0599, approximately 2.5 osy, comprised of nylon adhesively laminated to a breathable film laminate (1.0 osy). The texturized material, was ultrasonically welded to the necked bonded laminate. A commercially available baby toothpaste (GERBER) was then applied to the finger glove, which was subsequently used to clean the mouth of a toddler.

Example 21

A finger glove was constructed similar to the finger glove in Example 1. In contrast to Example 1, however, instead of using a stretch bonded laminate as the elastic material, a neck-bonded laminate was used. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width. In further contrast to Example 1, the texturized material was a needlepunched nonwoven substrate, with a basis weight of approximately 5 osy.

The texturized material was ultrasonically welded to the necked-bonded laminate. Peppermint oil was then applied to the finger glove, which was subsequently used to clean the mouth of an adult.

Example 22

The ability of a fastening mechanism of the present invention to be attached to a finger toothbrush was demonstrated. A finger toothbrush of the present invention was formed as follows. Specifically, a first section made from a point unbonded polypropylene spunbond material was ultrasonically welded to a stretch-bonded laminate (SBL) sheet using a Branson 920 IW ultrasonic welder. The point unbonded spunbond material formed the front of the toothbrush, while the SBL sheet formed the back of the toothbrush.

The point unbonded spunbond had a total basis weight of about 2.7 osy. The spunbond material was thermally bonded using a point-unbonded pattern that created texture. In particular, circular tufts were formed on the spunbond material. During bonding, a top bond roll having the point-unbonded pattern was heated to 330–360° F. while a bottom bond roll was heated to 300° F.

The SBL sheet, on the other hand, included threads of an elastic material sandwiched between two polypropylene spunbond layers. The elastic material used was KRATON G2740 S-EB-S block copolymer available from the Shell Oil Company. The SBL sheet had a basis weight of 2.5 osy. An imprinted, magnesium bond plate was used to bond the SBL sheet to the point unbonded spunbond material.

The resulting structure was in the shape of a finger, with a more rounded region at the top and straight sides tapering outwards, such that the interior width at 3.7 cm from the top was about 1.8 cm. Excess material was trimmed around the seam, leaving a textured finger toothbrush with a pull-on tab (SBL side).

A thin (0.6 cm) strip of SBL was formed into a ring (1.5 cm diameter) with a tail, and thermally bonded to close the ring. The end of the tail (5 cm) was thermally bonded to the pull-on tab of the finger toothbrush to produce a finger toothbrush with a tethered fastening ring. The toothbrush was treated with peppermint oil (5 microliters) and used by a small child.

Example 23

The ability of a finger glove of the present invention to be applied with an anti-ulcer component was demonstrated. A finger glove of the present invention was formed as follows. Specifically, a first section made from a point unbonded spunbond laminate material was ultrasonically welded to a stretch-bonded laminate (SBL) sheet using a Branson 920 IW ultrasonic welder. The point unbonded spunbond laminate formed the front of the finger glove, while the SBL sheet formed the back of the finger glove.

The point unbonded spunbond laminate was formed by thermally bonding together a first polypropylene spunbond web, a breathable film sheet, and a second polypropylene spunbond web. The breathable film sheet was placed in between the spunbond webs.

The first polypropylene spunbond web had a basis weight of 0.5 osy. The second polypropylene spunbond web had a basis weight of 2.8 osy with an average fiber diameter of 7.05 denier. The breathable film sheet was made from a linear low density polyethylene containing a calcium carbonate filler. The film was stretched in order to create a microporous film. The film had a basis weight of 0.5 osy.

The point unbonded spunbond laminate material was thermally bonded using a point-unbonded pattern that created texture. In particular, circular tufts were formed on the second polypropylene spunbond web side of the laminate. During bonding, a top bond roll having the point-unbonded pattern was heated to 350° F. while a bottom bond roll was heated to 300° F.

The SBL sheet, on the other hand, included threads of an elastic material sandwiched between two polypropylene spunbond layers. The elastic material used was KRATON G2740 S-EB-S block copolymer available from the Shell Oil Company. The SBL sheet had a basis weight of 2.5 osy. An imprinted, magnesium bond plate was used to bond the SBL sheet to the point unbonded spunbond laminate.

The second polypropylene spunbond layer of the point unbonded spunbond material was placed adjacent to the SBL sheet during the ultrasonic welding process, which placed the textured nubs against the SBL sheet. After ultrasonic welding, excess material was trimmed around the edges and the finger glove was inverted to place the seam on the inside and the textured nubs on the outside.

The resulting bonded wipe was in the shape of a finger having a rounded region at the top and straight sides tapering outwards, such that the width of the bond pattern 1 cm from the top was 2.3 cm, and the width at 4.5 cm from the top was 2.8 cm.

Thereafter, tetracycline hydrochloride and peppermint oil (20 microliters) were added to the finger glove. The tetracycline hydrochloride was obtained from Apothecon, a subsidiary of Bristol-Myers Squibb, in the form of a drug sold as SUMYCIN. The tetracycline hydrochloride was applied to the finger glove in the form of a solution containing 100 microliters of a 40 mg SUMYCIN/milliliter solution in water.

Example 24

The ability of a finger glove of the present invention to be applied with the following anti-ulcer component was demonstrated. The finger glove of Example 1 was treated with metronidazole and peppermint oil (20 microliters). Metronidazole was obtained in the form of a topical gel called METROGEL, which is commercially available from Galderma. 200 mg of METROGEL was applied to the finger glove, which thereby delivered 1.5 mg of metronidazole to the wipe.

Example 25

The ability of a finger glove of the present invention to be applied with the following anti-ulcer component was demonstrated. The finger glove of Example 1 was treated with bismuth subsalicylate which is the active ingredient in PEPTO-BISMOL sold by Procter and Gamble. 300 microliters of PEPTO-BISMOL was applied to the finger glove, which was subsequently used to clean the mouth of a user.

Example 26

The ability of a finger glove of the present invention to be applied with the following anti-ulcer components was demonstrated. The finger glove of Example 1 was treated with a suspension of bismuth subsalicylate (200 microliters of PEPTO-BISMOL), metronidazole (50 mg of METROGEL lotion), tetracycline (10 mg of SUMYCIN), and peppermint oil (20 microliters) were applied to the finger glove, which was then used to clean the mouth of a user.

Example 27

A point unbonded spunbond laminate material was formed by thermally fusing (using a point-unbonded pattern) three materials: a bicomponent spunbond web (PE/PP, side-by-side, 0.45 osy), a film (0.0007" CATALLOY film, supplied by Pliant Corporation), and a through-air bonded web (PE/PP, side-by-side, 3.5 osy), with bond pressure, line speed, and temperature adequate to sustain the desirable level of bonding and texture. In this case, the top patterned roll was heated to 256° F., while the bottom bond roll was heated to 248° F. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

An imprinted, stainless steel bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside. A peppermint flavoring (37 µL) was added to the finger glove, which was subsequently packaged in a laminated packaging material that substantially retained the flavoring over time. After one month, the package was opened and the product used to clean the mouth of an adult.

Example 28

A point unbonded spunbond laminate material was formed by thermally fusing (using a point-unbonded pattern) three materials: a bicomponent spunbond web (PE/PP, side-by-side, 0.45 osy), a film (0.0007" CATALLOY film, supplied by Pliant Corporation), and a through-air bonded web (PE/PP, side-by-side, 3.5 osy), with bond pressure, line speed, and temperature adequate to sustain the desirable level of bonding and texture. In this case, the top patterned roll was heated to 256° F., while the bottom bond roll was heated to 248° F. The resulting point unbonded spunbond laminate sheet was ultrasonically welded to a neck-bonded laminate (NBL) sheet using a Branson 920 IW ultrasonic welder. The neck-bonded laminate contained a 1.0 osy metllocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

An imprinted, stainless steel bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding).

After ultrasonic welding, excess material was trimmed around the edges, and the finger toothbrush was inverted to place the seam on the inside and the textured nubs on the outside. A suspension of encapsulated flavors in oil (200 mg of a suspension made up of 300 mg encapsulated wintergreen flavor, available from Flavors of North America, Inc., 220 mg encapsulated natural mint flavor, available from Flavors of North America, Inc., 120 mg xylitol, available from Cultor Corporation, and 2 g sunflower oil) was added to the finger toothbrush. The product was packaged, sealed, and then open 48 hours later to clean the mouth of an adult.

Example 29

Example Number 28 was repeated. Instead of using sunflower oil, however, the encapsulated flavors were combined with food-grade propylene glycol.

Example 30

A point unbonded spunbond laminate material was formed by ultrasonically fusing (using a point-unbonded pattern on a 2" rotary ultrasonic anvil) two materials: a film (0.0007" CATALLOY film, supplied by Pliant Corporation), and through-air bonded web (PE/PP, side-by-side, 3.8 osy), with bond pressure, power, and line speed adequate to sustain the desirable level of bonding and texture. The through-air bonded web was next to the patterned anvil during the bonding process. The resulting point unbonded spunbond laminate sheet was ultrasonically welded to a neck-bonded laminate (NBL) sheet using a Branson 290 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

An imprinted, stainless steel bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside. Peppermint oil was added to the finger glove, which was subsequently used to clean the mouth of an adult.

Example 31

A point unbonded spunbond laminate material was formed by ultrasonically fusing (using a point-unbonded pattern on a 2" rotary ultrasonic anvil) two materials: a breathable film sheet (LLDPE/CaCO$_3$/polypropylene, 1.0 osy) and a through-air bonded web (PE/PP, side-by-side fibers 3.5 osy), with bond pressure, line speed, and temperature adequate to sustain the desirable level of bonding and texture. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width. An imprinted, stainless steel bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside.

Example 32

A point unbonded spunbond laminate material was formed by ultrasonically fusing (using a point-unbonded pattern on a 2" rotary ultrasonic anvil) two through-air bonded webs. Both webs were comprised of bicomponent, PE/PP, side-by-side fibers. The top web, adjacent to the patterned anvil during bonding, was comprised of pentalobal shaped fibers, and had a basis weight of 3.5 osy. The bottom web was comprised of conventional round fibers, and had a basis weight of 3.8 osy. Bond pressure (60 psi) and line speed (80 fpm) were set to ensure adequate bonding, although adjustments to the power could allow for other settings providing nearly equivalent bonding. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width. An imprinted, magnesium bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside.

Example 33

A point unbonded spunbond laminate material was formed by ultrasonically bonding two through-air bonded webs. Both webs were comprised of bicomponent, PE/PP, side-by-side fibers. The depth of the round circles (corresponding the unbonded regions) in the patterned anvil was 0.060". The top web, adjacent to the patterned anvil during bonding, was comprised of pentalobal shaped fibers, and had a basis weight of 3.5 osy. The bottom web was comprised of conventional round fibers, and had a weight of 3.8 osy. Bond pressure (60 psi) and line speed (80 fpm) were set to ensure adequate bonding, although adjustments to the power could allow for other settings providing nearly equivalent bonding. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width. An imprinted, magnesium bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside.

Example 34

A point unbonded spunbond laminate material was formed by ultrasonically bonding two through-air bonded webs. Both webs were comprised of bicomponent, PE/PP, side-by-side fibers. The depth of the round circles (corresponding the unbonded regions) in the patterned anvil was 0.120". The top web, adjacent to the patterned anvil during bonding, was comprised of pentalobal shaped fibers, and had a basis weight of 3.5 osy. The bottom web was comprised of conventional round fibers, and had a basis weight of 3.8 osy. Bond pressure (60 psi) and line speed (80 fpm) were set to ensure adequate bonding, although adjustments to the power could allow for other settings providing nearly equivalent bonding. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a weight of 0.5 osy prior to being stretched or necked. The spunbond facings were necked to a width corresponding to 42% of their original width. An imprinted, magnesium bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside.

Example 35

A finger glove as described in Example 1 was constructed and used to apply petroleum jelly to an infant during a diaper change. In this example, however, the point unbonded spunbond laminate was replaced with a spunbond/meltblown/spunbond laminate. The laminate had a basis weight of 1.4 osy and was made entirely from polypropylene fibers. The laminate was ultrasonically welded to the stretch-bonded laminate described in Example 1.

In this example, the finger glove was inverted. The finger glove was then subsequently dipped in petroleum jelly, which was applied to an infant during a diaper change.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A finger glove comprising:
   a hollow member having an open end for the insertion of a finger, said hollow member comprising a first panel attached to a second panel, said first panel comprising a nonwoven material, said second panel comprising an elastic nonwoven material, said first panel being connected to said second panel in a manner that forms a seam.

2. A finger glove as defined in claim 1, wherein said first panel includes a texturized surface.

3. A finger glove as defined in claim 2, wherein said texturized surface comprises looped bristles.

4. A finger glove as defined in claim 2, wherein said texturized surface comprises a point unbonded material, said point unbonded material comprising a plurality of raised tufts surrounded by bonded regions.

5. A finger glove as defined in claim 1, wherein said elastic nonwoven material comprises a stretch bonded laminate.

6. A finger glove as defined in claim 1, wherein said elastic nonwoven material comprises a neck bonded laminate.

7. A finger glove as defined in claim 1, wherein said hollow member has been inverted such that said seam is located on the inside of said glove.

8. A finger glove as defined in claim 1, wherein said elastic nonwoven material comprises an elastic material positioned in between a first nonwoven web and a second nonwoven web.

9. A finger glove as defined in claim 1, wherein said nonwoven material comprises a laminate including a moisture barrier layer positioned in between a first nonwoven web and a second nonwoven web.

10. A finger glove comprising:
    a first panel attached to a second panel, said first panel and said second panel defining a pocket therebetween, said pocket having a distal end and a proximal end, said distal end being closed and said proximal end being open, said open proximal end being configured to allow the insertion of a finger into said pocket, said second panel comprising an elastic nonwoven material.

11. A finger glove as defined in claim 10, wherein said elastic nonwoven material comprises a material selected from the group consisting of stretch bonded laminates and neck bonded laminates.

12. A finger glove as defined in claim 10, wherein said elastic nonwoven material comprises a laminate.

13. A finger glove as defined in claim 10, wherein said elastic nonwoven material comprises an elastic material positioned in between a first nonwoven web and a second nonwoven web.

14. A finger glove as defined in claim 13, wherein said elastic material comprises a film.

15. A finger glove as defined in claim 13, wherein said elastic material comprises elastic strands.

16. A finger glove as defined in claim 13, wherein said second panel comprises a non-elastic nonwoven material.

17. A finger glove comprising:
    a hollow member having an open end for the insertion of a finger, said hollow member comprising a first panel attached to a second panel, said first panel comprising a non-elastic nonwoven material containing fibers made from a thermoplastic polymer, said second panel comprising a elastic nonwoven material that allows said hollow member to be stretched and contracted for providing said hollow member with form-fitting properties.

18. A finger glove as defined in claim 17, wherein said first panel is connected to said second panel in a manner that forms a seam, said hollow member being inverted such that said seam is located on the inside of said glove.

19. A finger glove as defined in claim 17, further comprising a moisture barrier layer incorporated into at least a portion of one of said first or said second panels.

20. A finger glove as defined in claim 17, wherein said open end is configured to receive two fingers of a user.

21. A finger glove as defined in claim 17, wherein said non-elastic nonwoven material comprises a laminate including a moisture barrier layer positioned in between a first nonwoven web and a second nonwoven web.

22. A finger glove as defined in claim 17, wherein said non-elastic nonwoven material comprises a material selected from the group consisting of spunbonded webs, meltblown webs, spunbonded/meltblown/spunbonded webs, through air bonded webs, spunbonded/meltblown webs, and bonded carded webs.

23. A finger glove as defined in claim 17, wherein said first panel defines a texturized surface, said texturized surface comprising a material selected from the group consisting of looped bristles, crimped fibers, and a point unbonded material containing a plurality of tufts surrounded by bonded regions.

24. A finger glove as defined in claim 23, wherein said texturized surface comprises said point unbonded material, said tufts contained in said point unbonded material having a height of at least 0.02 inches.

25. A finger glove comprising:

a hollow member having an open end for the insertion of a finger, said hollow member comprising a first panel thermally bonded to a second panel thereby forming a seam, said first panel comprising a non-elastic material containing a nonwoven web, said second panel comprising an elastic nonwoven material, said elastic nonwoven material being capable of being stretched and contracted for providing said finger glove with form fitting properties.

26. A finger glove as defined in claim 25, wherein said first panel further comprises a texturized surface.

27. A finger glove as defined in claim 25, wherein said non-elastic material comprises a material selected from the group consisting of spunbonded webs, meltblown webs, spunbonded/meltblown/spunbonded webs, spunbonded/meltblown webs, through air bonded webs and bonded carded webs.

28. A finger glove as defined in claim 25, wherein said non-elastic material comprises a laminate including a moisture barrier positioned in between a first nonwoven web and a second nonwoven web.

29. A finger glove as defined in claim 28, wherein said elastic nonwoven material comprises an elastic material positioned in between a pair of nonwoven webs.

30. A finger glove as defined in claim 25, wherein said hollow member is inverted such that said seam is located on the inside of said glove.

* * * * *